(12) United States Patent
Kitamura et al.

(10) Patent No.: US 9,179,822 B2
(45) Date of Patent: Nov. 10, 2015

(54) ENDOSCOPIC OBSERVATION SUPPORTING SYSTEM, METHOD, DEVICE AND PROGRAM

(75) Inventors: Yoshiro Kitamura, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 447 days.

(21) Appl. No.: 13/582,603

(22) PCT Filed: Mar. 16, 2011

(86) PCT No.: PCT/JP2011/001563
§ 371 (c)(1),
(2), (4) Date: Sep. 4, 2012

(87) PCT Pub. No.: WO2011/114731
PCT Pub. Date: Sep. 22, 2011

(65) Prior Publication Data
US 2012/0327186 A1    Dec. 27, 2012

(30) Foreign Application Priority Data
Mar. 17, 2010    (JP) .................... 2010-060285

(51) Int. Cl.
*A61B 1/00*    (2006.01)
*A61B 5/06*    (2006.01)
*A61B 6/00*    (2006.01)

(52) U.S. Cl.
CPC ......... *A61B 1/00009* (2013.01); *A61B 1/00045* (2013.01); *A61B 1/00193* (2013.01); *A61B 5/064* (2013.01); *A61B 6/5247* (2013.01)

(58) Field of Classification Search
CPC ............. A61B 1/0005; A61B 1/00009; A61B 2019/507; A61B 19/5212; A61B 19/5244; A61B 19/56; A61B 19/2019; A61B 19/5291; A61B 6/032; A61B 1/00193; A61B 1/042; A61B 2019/5289; A61B 5/065; A61B 6/022; A61B 6/461; A61B 8/08; A61B 8/483; G06T 19/003; G06T 15/00; H04N 13/0055
USPC .................... 348/45, 166; 382/128; 434/262; 600/111, 116
See application file for complete search history.

(56) References Cited

U.S. PATENT DOCUMENTS 6,016,439 A    1/2000    Acker
6,167,296 A    12/2000    Shahidi
(Continued)

FOREIGN PATENT DOCUMENTS

JP    11-000309    1/1999
JP    2002-263053    9/2002
(Continued)

OTHER PUBLICATIONS

International Search Report, PCT/JP2011/001563, Jun. 7, 2011.
(Continued)

*Primary Examiner* — Brian Yenke
(74) *Attorney, Agent, or Firm* — Young & Thompson

(57) ABSTRACT

A virtual endoscopic image generating unit for generating, from a 3D medical image representing an interior of a body cavity of a subject formed by a 3D medical image forming unit and inputted thereto, a virtual endoscopic image, in which a position of a structure of interest identified by a position of interest identifying unit is a view point of the virtual endoscopic image, a real-time position of at least one of an endoscope and a surgical tool detected by an endoscope position detecting unit or a surgical tool position detecting unit is contained in a field of view of the virtual endoscopic image, and the position of at least one of the endoscope and the surgical tool is shown in an identifiable manner in the virtual endoscopic image, is provided. A display control unit causes a WS display to display the generated virtual endoscopic image.

14 Claims, 15 Drawing Sheets

(56) References Cited

U.S. PATENT DOCUMENTS

| | | | |
|---|---|---|---|
| 6,346,940 B1* | 2/2002 | Fukunaga | 345/427 |
| 8,611,998 B2* | 12/2013 | Pastore et al. | 607/9 |
| 8,670,816 B2* | 3/2014 | Green et al. | 600/424 |
| 8,672,836 B2* | 3/2014 | Higgins et al. | 600/117 |
| 8,731,367 B2* | 5/2014 | Sakaguchi | 386/223 |
| 8,744,149 B2* | 6/2014 | Nakamura | 382/128 |
| 2002/0128547 A1 | 9/2002 | Furuhashi et al. | |
| 2003/0152897 A1* | 8/2003 | Geiger | 434/262 |
| 2005/0033117 A1 | 2/2005 | Ozaki et al. | |
| 2005/0187432 A1* | 8/2005 | Hale et al. | 600/117 |
| 2006/0004286 A1* | 1/2006 | Chang et al. | 600/435 |
| 2007/0135803 A1* | 6/2007 | Belson | 606/1 |
| 2007/0173689 A1 | 7/2007 | Ozaki et al. | |
| 2008/0207997 A1* | 8/2008 | Higgins et al. | 600/114 |
| 2009/0259102 A1* | 10/2009 | Koninckx et al. | 600/111 |
| 2011/0137156 A1* | 6/2011 | Razzaque et al. | 600/424 |
| 2011/0245660 A1* | 10/2011 | Miyamoto | 600/424 |
| 2012/0113111 A1* | 5/2012 | Shiki et al. | 345/419 |
| 2012/0136208 A1* | 5/2012 | Itai | 600/109 |

FOREIGN PATENT DOCUMENTS

| | | |
|---|---|---|
| JP | 2005-021353 | 1/2005 |
| JP | 2005-211529 | 8/2005 |
| JP | 2006-198032 | 8/2006 |
| JP | 2007-029232 | 2/2007 |

OTHER PUBLICATIONS

Supplementary European Search Report dated Aug. 21, 2013 in corresponding European Application No. 11755922.

* cited by examiner

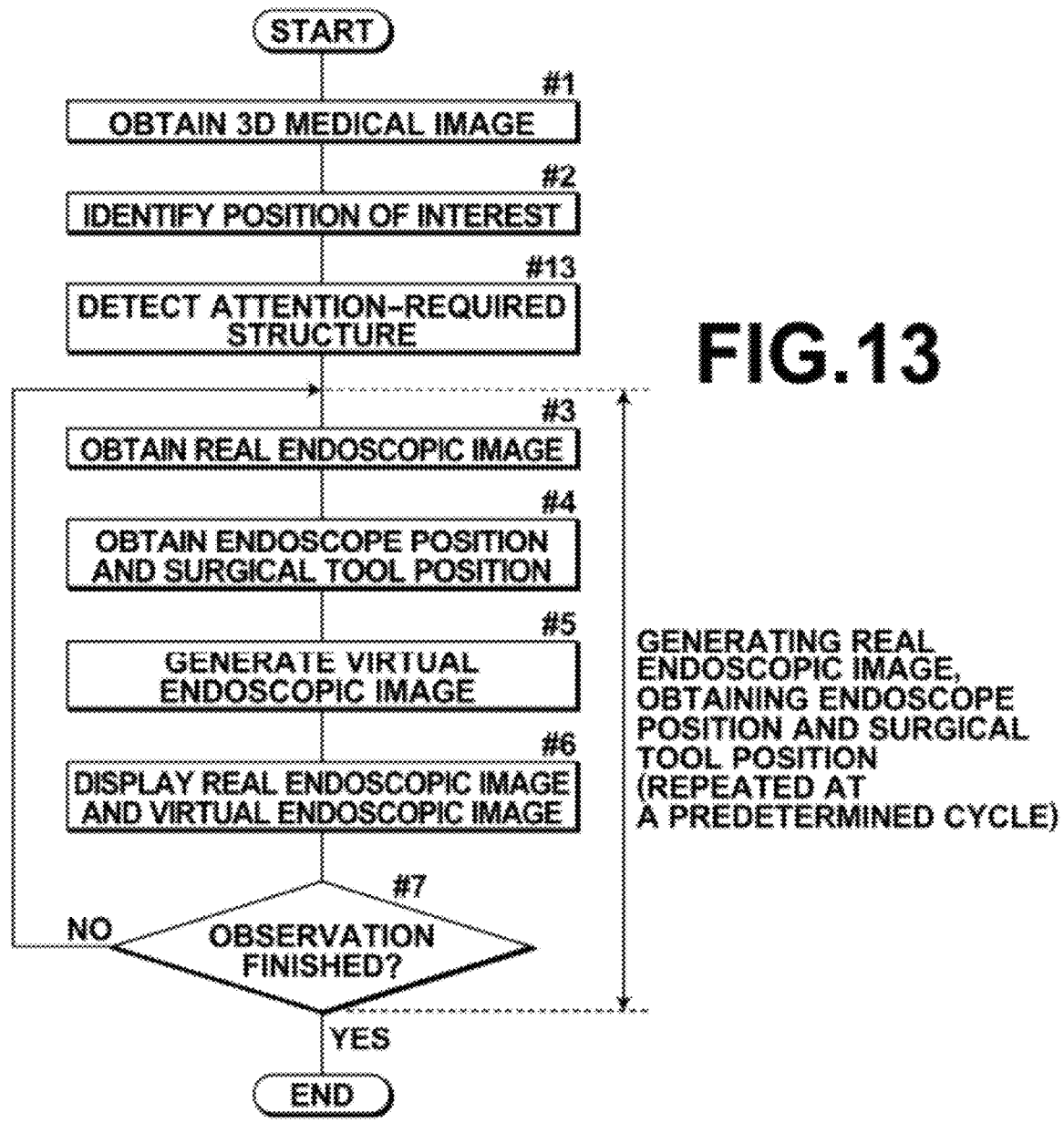

ENDOSCOPIC OBSERVATION SUPPORTING SYSTEM, METHOD, DEVICE AND PROGRAM

BACKGROUND OF THE INVENTION

1. Field of the Invention

The present invention relates to a technology for supporting endoscopic observation during surgery or examination using an endoscope inserted in a body cavity of a subject, and in particular to a technology for supporting endoscopic observation using a virtual endoscopic image representing the interior of a body cavity of a subject.

2. Description of the Related Art

In recent years, surgery using an endoscope, such as laparoscopic surgery and thoracoscopic surgery, is drawing attention. The endoscopic surgery is advantageous in that it does not require laparotomy, thoracotomy, or the like, and only needs to make two or three holes of few centimeters in diameter for insertion of an endoscope and a surgical tool, thereby significantly reducing the burden imposed on the patient. However, conducting surgery with a very limited field of view of the endoscope is highly difficult, and doctors require a lot of skill to conduct the endoscopic surgery. If a blood vessel or an organ of the patient is damaged by mistake and breeds during the endoscopic surgery, it is impossible to continue the endoscopic surgery and the doctor has to conduct conventional surgery involving laparotomy, thoracotomy, or the like.

On the other hand, a virtual endoscopy technology for generating a virtual endoscopic image, which is similar to an endoscopic image, from a 3D volume image taken with a CT device, or the like, is known. This technology is widely used in North America as a method for finding a tumor, in particular, a colorectal tumor, only by CT imaging without conducting endoscopic examination.

Further, a technology for supporting endoscopic surgery using a virtual endoscopic image has been proposed.

For example, Japanese Unexamined Patent Publication No. 2002-263053 (hereinafter, Patent Document 1) has disclosed a device that detects a position of an endoscope with a sensor, generates a virtual endoscopic image having an angle of view wider than that of the endoscope with setting the detected position of the endoscope as a view point, and displays the virtual endoscopic image and a real endoscopic image taken with the endoscope superimposed one on the other.

Further, Japanese Unexamined Patent Publication No. 2005-021353 (hereinafter, Patent Document 2) has disclosed a device that detects a real-time position of an endoscope to generate a virtual endoscopic image having the same field of view as that of the endoscope, where location of blood vessels in the field of view is visualized. The device also detects a real-time position of a surgical tool used during endoscopic surgery to generate a composite image in which an image representing the surgical tool is combined at the position of the surgical tool in the virtual endoscopic image, and displays the composite image and a real endoscopic image.

The virtual endoscopic image according to the techniques disclosed in these documents, however, has the same view point as that of the real endoscopic image, i.e., is an image viewed from the same observation direction as that of the real endoscopic image. Therefore, depending on the positional relationship between a site of interest, such as a site of surgical interest, and the endoscope or the surgical tool, the site of interest may sometimes not be shown in the virtual endoscopic image or the real endoscopic image, and the doctor cannot recognize the approach of the endoscope or the surgical tool to the site of interest in such a case.

SUMMARY OF THE INVENTION

In view of the above-described circumstances, the present invention is directed to providing a system, a method, a device and a program for allowing the user to recognize the approach of an endoscope or a surgical tool to a site of interest, such as a site of surgical interest, more reliably during observation of a body cavity of a subject using the endoscope inserted in the body cavity.

An aspect of an endoscopic observation support system of the invention is an endoscopic observation support system comprising: 3D medical image forming means for forming a 3D medical image representing an interior of a body cavity of a subject; position of interest identifying means for identifying a position of a (first) structure of interest in the body cavity in the 3D medical image; position detecting means for detecting a real-time position of at least one of an endoscope and a surgical tool inserted in the body cavity; virtual endoscopic image generating means for generating, from the 3D medical image inputted thereto, a virtual endoscopic image representing the interior of the body cavity viewed from a view point, based on the identified position of the (first)) structure of interest and the detected position of at least one of the endoscope and the surgical tool in the 3D medical image, wherein the view point is the position of the (first) structure of interest, the position of at least one of the endoscope and the surgical tool is contained in a field of view of the virtual endoscopic image, and the position of at least one of the endoscope and the surgical tool is shown in an identifiable manner in the virtual endoscopic image; and display means for displaying the virtual endoscopic image.

An aspect of an endoscopic observation support method of the invention is an endoscopic observation support method comprising the steps of: forming a 3D medical image representing an interior of a body cavity of a subject before or during observation of the interior of the body cavity with an endoscope inserted in the body cavity; identifying a position of a (first) structure of interest in the body cavity in the 3D medical image; detecting a real-time position of at least one of the endoscope and a surgical tool inserted in the body cavity; generating, from the 3D medical image inputted, a virtual endoscopic image representing the interior of the body cavity viewed from a view point, based on the identified position of the (first) structure of interest and the detected position of at least one of the endoscope and the surgical tool in the 3D medical image, wherein the view point is the position of the (first) structure of interest, the position of at least one of the endoscope and the surgical tool is contained in a field of view of the virtual endoscopic image, and the position of at least one of the endoscope and the surgical tool is shown in an identifiable manner in the virtual endoscopic image; and displaying the virtual endoscopic image.

An aspect of an endoscopic observation support device of the invention is an endoscopic observation support device comprising: 3D medical image obtaining means for obtaining a 3D medical image representing an interior of a body cavity of a subject; position of interest identifying means for identifying a position of a (first) structure of interest in the body cavity in the 3D medical image; position obtaining means for obtaining a real-time position of at least one of an endoscope and a surgical tool inserted in the body cavity detected by position detecting means; virtual endoscopic image generating means for generating, from the 3D medical image inputted thereto, a virtual endoscopic image representing the interior of the body cavity viewed from a view point, based on the identified position of the (first) structure of interest and the detected position of at least one of the endoscope and the surgical tool in the 3D medical image, wherein the viewpoint is the position of the (first) structure of interest, the position of at least one of the endoscope and the surgical tool is contained in a field of view of the virtual endoscopic image, and the position of at least one of the endoscope and the surgical tool is shown in an identifiable manner in the virtual endoscopic image; and display control means for causing display means to display the virtual endoscopic image.

An aspect of an endoscopic observation support program of the invention is an endoscopic observation support program for causing a computer to carry out the steps of: obtaining a 3D medical image representing an interior of a body cavity of a subject; identifying a position of a (first) structure of interest in the body cavity in the 3D medical image; obtaining a real-time position of at least one of an endoscope and a surgical tool inserted in the body cavity detected by position detecting means; generating, from the 3D medical image inputted, a virtual endoscopic image representing the interior of the body cavity viewed from a view point, based on the identified position of the (first) structure of interest and the detected position of at least one of the endoscope and the surgical tool in the 3D medical image, wherein the view point is the position of the (first) structure of interest, the position of at least one of the endoscope and the surgical tool is contained in a field of view of the virtual endoscopic image, and the position of at least one of the endoscope and the surgical tool is shown in an identifiable manner in the virtual endoscopic image; and causing display means to display the real endoscopic image and the virtual endoscopic image.

Now, details of the invention are described.

In the invention, a real endoscopic image representing the interior of body cavity may be formed by real-time imaging with the endoscope, and the real endoscopic image which is formed almost at the same time when the position of at least one of the endoscope and the surgical tool used to generate the virtual endoscopic image is detected may further be displayed. In this manner, the real endoscopic image formed real-time by imaging with the endoscope and the virtual endoscopic image, which contains, in the field of view thereof, the real-time position of at least one of the endoscope and the surgical tool detected by the position detecting means almost at the same time when the real endoscopic image is formed, are displayed.

In a case where generation of the virtual endoscopic image is repeated in response to detection of the position of at least one of the endoscope and the surgical tool, real-time update of both the real endoscopic image and the virtual endoscopic image is achieved.

The real endoscopic image and the virtual endoscopic image may be displayed on a single display device or may be displayed separately on a plurality of display devices. The plurality of display devices may be located side by side at the physically same place so that both the images can be observed simultaneously, or may be located at places physically apart from each other so that the images are observed separately.

In the invention, in a case where the 3D medical image is obtained during observation using the endoscope, the 3D medical image may be obtained real-time. In this case, the position of at least one of the endoscope and the surgical tool may be detected by performing image recognition processing on the obtained 3D medical image.

Specific examples of the "(first) structure of interest" may include a site of surgical interest during endoscopic surgery and an anatomical structure that requires attention during endoscopic surgery, such as a blood vessel, an organ or a tumor. A specific method for identifying the position of the (first) structure of interest may be an automatic method using a known image recognition technique, a method involving manual operation by the user, or a method combining both the automatic and manual methods.

In the invention, a plurality of virtual endoscopic images may be generated by setting a plurality of positions of the (first) structure of interest as the view points.

The description "detecting . . . a position of at least one of an endoscope and a surgical tool" may refer to either of detecting the position of the endoscope when only the endoscope is inserted in the body cavity, or detecting the position of the endoscope, the position of the surgical tool, or both the positions of the endoscope and the surgical tool when the endoscope and the surgical tool are inserted in the body cavity.

The view point of the "virtual endoscopic image" is the position of the (first) structure of interest. However, the position of the view point is not strictly limited to a position on the surface of the (first) structure of interest or a position within the structure, and may be a position where an effect that is substantially equivalent to the effect of the invention is obtained, such as a position apart from the (first) structure of interest by few pixels.

The "virtual endoscopic image" contains the position of at least one of the endoscope and the surgical tool within the field of view thereof. This means that image information along a line of sight from the view point (the position of the (first) structure of interest) toward the position of at least one of the endoscope and the surgical tool is reflected in the virtual endoscopic image. If, for example, a structure, such as an organ, a blood vessel or a fold, is present between the (first) structure of interest and the endoscope or the surgical tool, the endoscope or the surgical tool may not necessarily be shown in the virtual endoscopic image.

Further, in the "virtual endoscopic image", the position of at least one of the endoscope and the surgical tool is shown in an identifiable manner. In a case where the 3D medical image is obtained before the endoscopic observation, the endoscope or the surgical tool has not yet been inserted in the body cavity of the subject when the 3D medical image is taken and obtained. Therefore, when the virtual endoscopic image is generated, a marker, or the like, representing the endoscope or the surgical tool may be combined at a position in the virtual endoscopic image corresponding to the position detected by the position detecting means. On the other hand, in a case where the 3D medical image is obtained real-time during the endoscopic observation and the endoscope or the surgical tool is shown in the image, the virtual endoscopic image may be generated such that the endoscope or the surgical tool is also shown in the virtual endoscopic image.

When the "virtual endoscopic image" is generated, a distance from the structure of interest to a surface of a structure in the body cavity may be used as a determinant of pixel values of the virtual endoscopic image. Alternatively, a color template, which is defined to provide the virtual endoscopic image showing sites in the body cavity in almost the same appearance as those shown in the real endoscopic image, may be used. It should be noted that the color template may include, for example, one that is defined such that each site in the body cavity has almost the same color of as that shown in the real endoscopic image, and each site in the body cavity may be shown semitransparent, as necessary, so that a structure behind an obstacle, which cannot be observed in the real endoscopic image, is visually recognizable in the virtual endoscopic image.

In the invention, a second structure of interest in the body cavity in the 3D medical image may be detected, and the virtual endoscopic image showing the detected second structure of interest in a visually recognizable manner may be generated. Specific examples of the "second structure of interest" may include those mentioned above with respect to the first structure of interest. Therefore, for example, the first structure may be a site of surgical interest during endoscopic surgery and the second structure of interest may be an anatomical structure that requires attention during the surgery, or vice versa.

In the invention, a warning may be shown when an approach of at least one of the endoscope and the surgical tool to the structure of interest satisfies a predetermined criterion. The warning may be visually shown in the virtual endoscopic image, or may be shown in a manner perceived by any other sense organ.

According to the invention, a 3D medical image representing an interior of a body cavity of a subject is obtained, a position of a structure of interest in the body cavity in the 3D medical image is identified, and a real-time position of at least one of an endoscope and a surgical tool inserted in the body cavity is detected. Then, from the 3D medical image inputted, a virtual endoscopic image is generated, wherein the view point of the virtual endoscopic image is the position of the structure of interest, the position of at least one of the endoscope and the surgical tool is contained in the field of view of the virtual endoscopic image, and the position of at least one of the endoscope and the surgical tool is shown in an identifiable manner in the virtual endoscopic image, and the virtual endoscopic image is displayed. The displayed virtual endoscopic image looks like an image taken with a camera that monitors the approach of the endoscope and the surgical tool to the structure of interest, such as a site of surgical interest or a site that requires attention. This virtual endoscopic image unique to the present invention compensates for the narrow field of view of the real endoscopic image, thereby allowing the user to more reliably recognize the approach of the endoscope or the surgical tool to the structure of interest and helping to prevent misoperation, etc., during surgery or examination.

Further, at this time, the field of view of the virtual endoscope of the continuously displayed virtual endoscopic image is changed real-time by feedback of the detected real-time position of the endoscope or the surgical tool. This allows the user to dynamically and more appropriately recognize the approach of the endoscope or the surgical tool to the structure of interest.

Still further, in the case where the real endoscopic image representing the interior of body cavity is formed by real-time imaging with the endoscope, and the real endoscopic image which is formed almost at the same time when the position of at least one of the endoscope and the surgical tool used to generate the virtual endoscopic image is detected is further displayed, the displayed real endoscopic image and virtual endoscopic image show the state of the interior of the body cavity almost at the same point of time, and the real endoscopic image and the virtual endoscopic image are continuously displayed in a temporally synchronized manner. Yet further, in the case where generation of the virtual endoscopic image is repeated in response to detection of the position of at least one of the endoscope and the surgical tool, real-time update of both the real endoscopic image and the virtual endoscopic image is achieved. That is, the field of view of the real endoscopic image changes along with movement or rotation of the endoscope, and the field of view of the virtual endoscopic image changes along with movement of the endoscope or the surgical tool. In this manner, the user can observe the interior of body cavity with complementarily using the real endoscopic image and the virtual endoscopic image.

BRIEF DESCRIPTION OF THE DRAWINGS

FIG. 13 is a flow chart illustrating the flow of the endoscopic observation support process according to the fifth embodiment of the invention.

DESCRIPTION OF THE PREFERRED EMBODIMENTS

Hereinafter, an endoscopic observation support system according to embodiments of the present invention is described.

Figure 1:
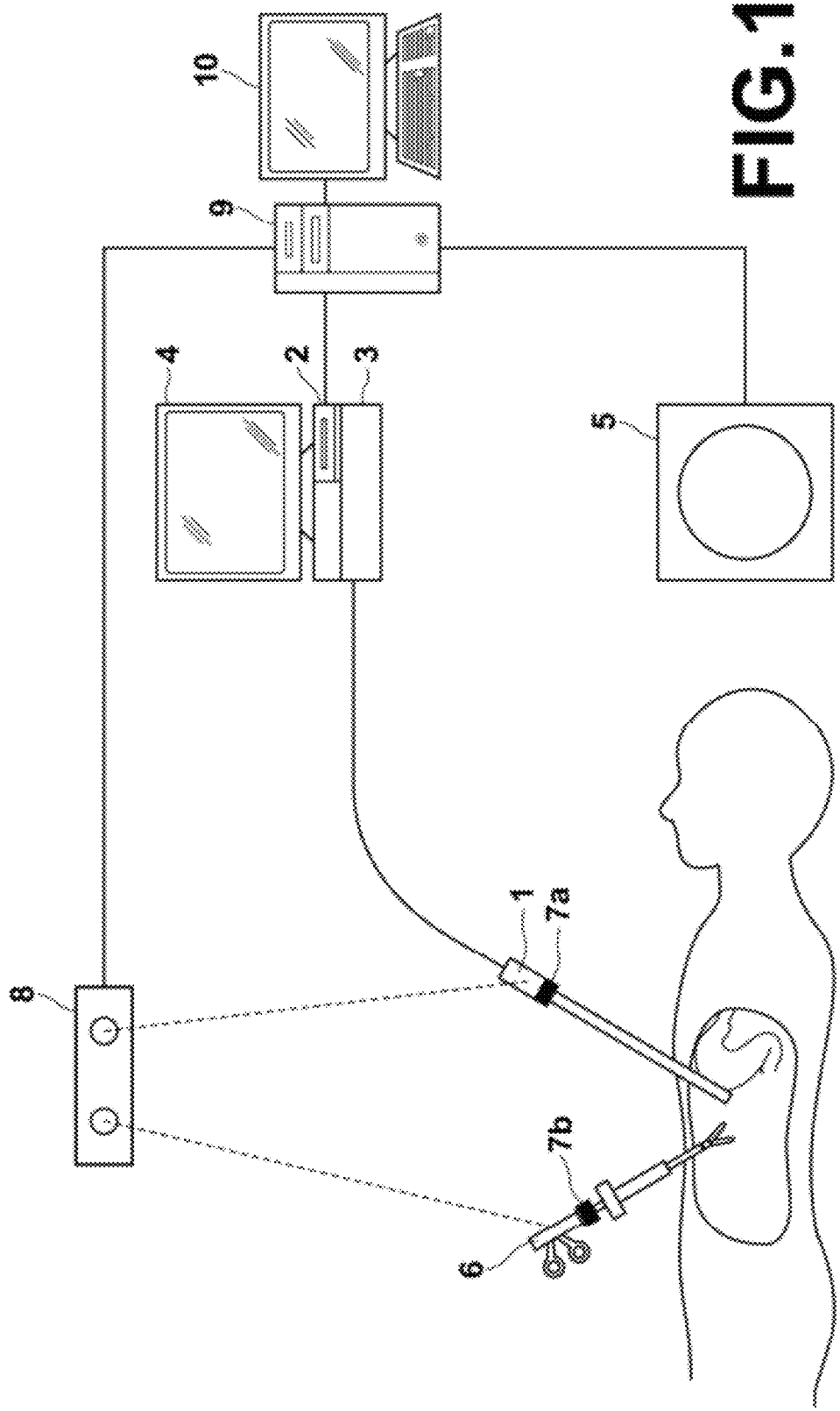
FIG. 1 is a hardware configuration diagram of an endoscopic observation support system according to embodiments of the present invention.

FIG. 1 is a hardware configuration diagram illustrating the outline of the endoscopic observation support system. As shown in the drawing, the system includes an endoscope 1, a digital processor 2, a light source device 3, a real endoscopic image display 4, a modality 5, a surgical tool 6, an endoscope marker 7a, a surgical tool marker 7b, a position sensor 8, an image processing workstation 9, and an image processing workstation display (which will hereinafter be referred to as "WS display") 10.

In this embodiment, the endoscope 1 is a hard endoscope for the abdominal cavity, and is inserted into the abdominal cavity of a subject. Light from the light source device 3 is guided by an optical fiber and emitted from the tip portion of the endoscope 1, and an image of the interior of the abdominal cavity of the subject is taken by an imaging optical system of the endoscope 1. The digital processor 2 converts an image signal obtained by the endoscope 1 into a digital image signal, and performs image quality correction by digital signal processing, such as white balance control and shading correction. Then, the digital processor 2 adds accompanying information prescribed by the DICOM (Digital Imaging and Communications in Medicine) standard to the digital image signal to output real endoscopic image data ($I_{RE}$). The outputted real endoscopic image data ($I_{RE}$) is sent to the image processing workstation 9 via a LAN according to a communication protocol conforming to the DICOM standard. Further, the digital processor 2 converts the real endoscopic image data ($I_{RE}$) into an analog signal and outputs the analog signal to the real endoscopic image display 4, so that the real endoscopic image ($I_{RE}$) is displayed on the real endoscopic image display 4. The endoscope 1 obtains the image signal at a predetermined frame rate, and therefore the real endoscopic image ($I_{RE}$) displayed on the real endoscope display 4 is a moving image showing the interior of the abdominal cavity. The endoscope 1 can also take a still image in response to an operation by the user.

The modality 5 is a device that images a site to be examined of the subject and generates image data (V) of a 3D medical image representing the site. In this embodiment, the modality 5 is a CT device. The 3D medical image data (V) also has the accompanying information prescribed by the DICOM standard added thereto. The 3D medical image data (V) is also sent to the image processing workstation 9 via the LAN according to the communication protocol conforming to the DICOM standard.

The endoscope marker 7a, the surgical tool marker 7b and the position sensor 8 form a known three-dimensional position measurement system. The endoscope marker 7a and the surgical tool marker 7b are provided in the vicinity of handles of the endoscope 1 and the surgical tool 6, respectively, and three-dimensional positions of the markers 7a, 7b are detected by the optical position sensor 8 at predetermined time intervals. Each of the endoscope marker 7a and the surgical tool marker 7b is formed by a plurality of marker chips, so that the position sensor 8 can also detect the orientation of each of the endoscope 1 and the surgical tool 6 based on a positional relationship among the marker chips, and three-dimensional positions ($PS_E$, $PS_T$) of the tip portions of the endoscope 1 and the surgical tool 6 may be calculated by an offset calculation. The position sensor 8 sends the calculated three-dimensional position data ($PS_E$, $PS_T$) of the endoscope 1 and the surgical tool 6 to the image processing workstation 9 via a USB interface.

The image processing workstation 9 is a computer having a known hardware configuration including a CPU, a main storage device, an auxiliary storage device, an input/output interface, a communication interface, a data bus, etc., to which an input device (such as a pointing device and a keyboard) and the WS display 10 are connected. The image processing workstation 9 is connected to the digital processor 2 and the modality 5 via the LAN, and to the position sensor 8 via the USB connection. The image processing workstation 9 has installed therein a known operating system, various application software programs, etc., and an application software program for executing an endoscopic observation support process of the invention. These software programs may be installed from a recording medium, such as a CD-ROM, or may be downloaded from a storage device of a server connected via a network, such as the Internet, before being installed.

Figure 2:
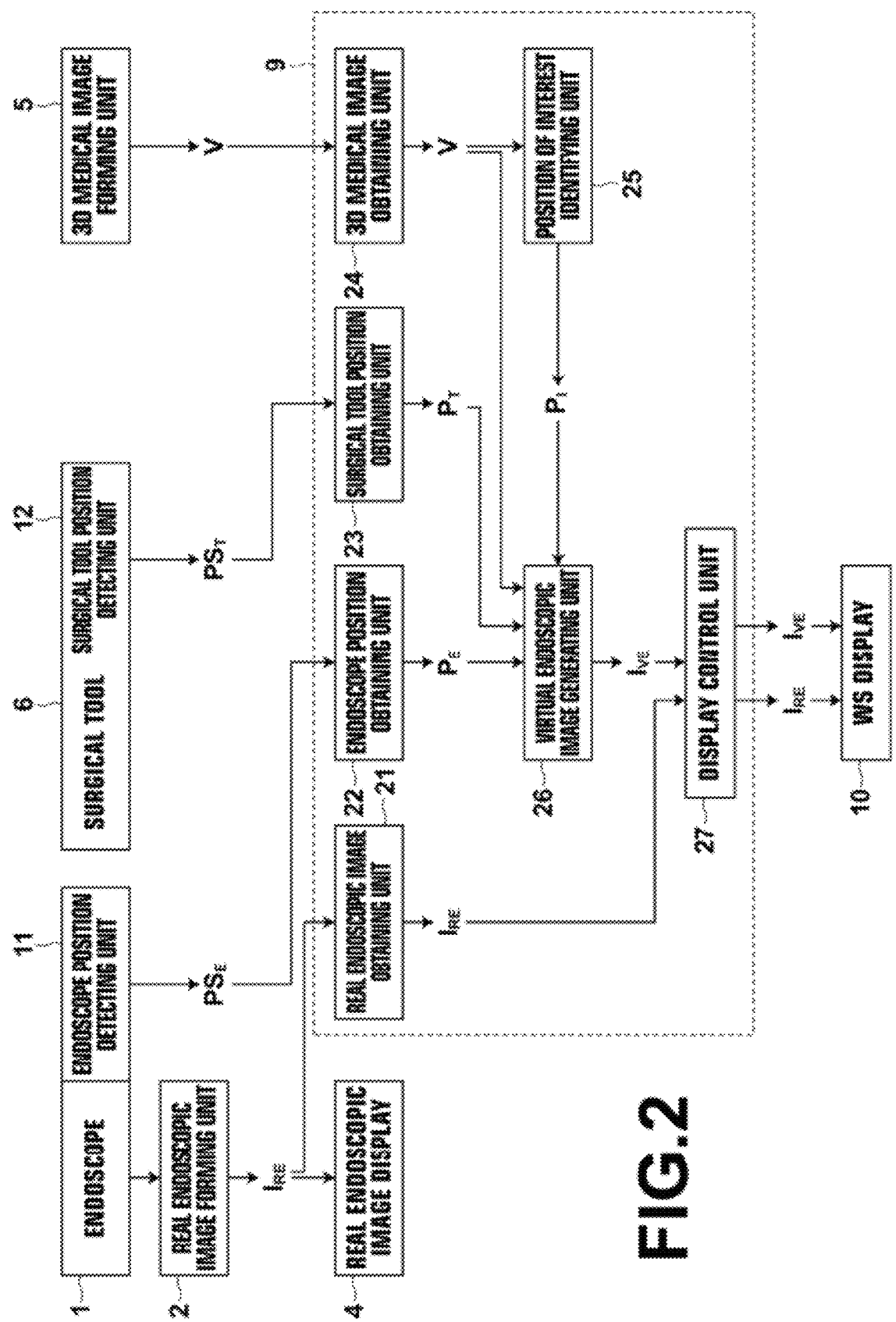
FIG. 2 is a functional block diagram of the endoscopic observation support system according to first to third embodiments of the invention.

FIG. 2 is a functional block diagram of the endoscopic observation support system according to a first embodiment of the invention. As shown in the drawing, the endoscopic observation support system according to the first embodiment of the invention includes the endoscope 1, a real endoscopic image forming unit 2, the real endoscopic image display 4, a 3D medical image forming unit 5, the surgical tool 6, the WS display 10, an endoscope position detecting unit 11, a surgical tool position detecting unit 12, a real endoscopic image obtaining unit 21, an endoscope position obtaining unit 22, a surgical tool position obtaining unit 23, a 3D medical image obtaining unit 24, a position of interest identifying unit 25, a virtual endoscopic image generating unit 26, and a display control unit 27. It should be noted that the same reference numeral as that assigned to the hardware device shown in FIG. 1 is used to denote a corresponding functional block shown in FIG. 2 when there is substantially one to one correspondence between them. That is, the function of the real endoscopic image forming unit 2 is implemented by the digital processor shown in FIG. 1, and the function of the 3D medical image forming unit 5 is implemented by the modality shown in FIG. 1. On the other hand, the function of the endoscope position detecting unit 11 is implemented by the endoscope marker 7a and the position sensor 8, and the function of the surgical tool position detecting unit 12 is implemented by the surgical tool marker 7b and the position sensor 8. The dashed line frame represents the image processing workstation 9, and the functions of the individual processing units in the dashed line frame are implemented by executing predetermined programs on the image processing workstation 9. Further, a real endoscopic image $I_{RE}$, an endoscope position $P_E$, a surgical tool position $P_T$, a 3D medical image V, a position of interest $P_I$ and a virtual endoscopic image $I_{VE}$ in the dashed line frame are data written in and read from predetermined memory areas of the image processing workstation 9 by the individual processing units in the dashed line frame.

Figure 3:
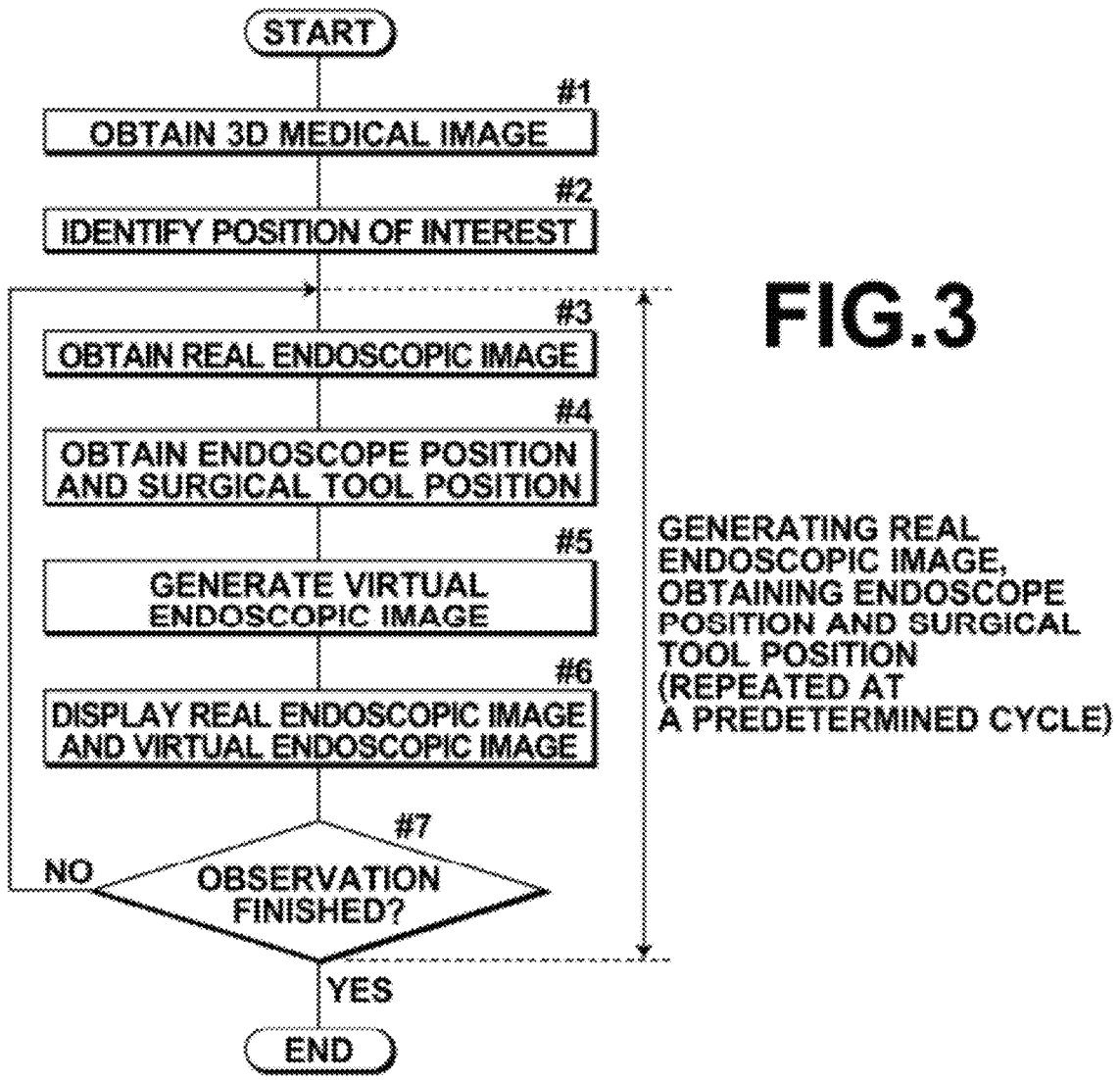
FIG. 3 is a flow chart illustrating the flow of an endoscopic observation support process according to the first to third embodiments of the invention.

Next, using the flow chart shown in FIG. 3, a schematic flow of operations by the user performed on the endoscopic observation support system and operations performed by the above-mentioned individual processing units according to the first embodiment of the invention is described.

Prior to observation of the interior of the abdominal cavity of a subject using the endoscope 1, the 3D medical image forming unit 5 images the interior of the abdominal cavity of the subject to form the 3D medical image V. On the image processing workstation 9, the 3D medical image obtaining unit 24 obtains the 3D medical image V formed by the 3D medical image forming unit 5 (#1), and then the position of interest identifying unit 25 shows a user interface for receiving a user operation to specify a structure of interest (for example, a site of surgical interest) in the body cavity shown in the 3D medical image V obtained by the 3D medical image obtaining unit 24, and identifies the position $P_I$ of the specified structure of interest in the 3D medical image V based on the obtained 3D medical image V (#2).

Then, as written on the right side of the flow chart shown in FIG. 3, during endoscopic surgery of the structure of interest, i.e., during observation of the interior of the abdominal cavity of the subject using the endoscope 1, the real endoscopic image forming unit 2 repeatedly forms the real endoscopic image $I_{RE}$ taken with the endoscope 1 inserted in the body cavity at a predetermined frame rate, and the formed real endoscopic image $I_{RE}$ is displayed real-time as a live-view image on the real endoscopic image display 4 until the observation is finished (#7: YES). Further, the endoscope position detecting unit 11 and the surgical tool position detecting unit 12 repeatedly detect the real-time positions $PS_E$, $PS_T$ of the endoscope 1 and the surgical tool 6 inserted in the body cavity at predetermined time intervals.

On the image processing workstation 9, the real endoscopic image obtaining unit 21 obtains the real endoscopic image $I_{RE}$ formed by the real endoscopic image forming unit 2 (#3). Almost at the same time with this, the endoscope position obtaining unit 22 obtains the endoscope position $PS_E$ detected by the endoscope position detecting unit 11 and outputs the endoscope position $P_E$, which is obtained by converting the obtained endoscope position $PS_E$ into a position in the coordinate system of the 3D medical image V, and the surgical tool position obtaining unit 23 obtains the surgical tool position $PS_T$ detected by the surgical tool position detecting unit 12 and outputs the surgical tool position $P_T$, which is obtained by converting the obtained surgical tool position $PS_T$ into a position in the coordinate system of the 3D medical image V (#4).

The virtual endoscopic image generating unit 26 generates, from the 3D medical image V obtained by the 3D medical image obtaining unit 24 and inputted thereto, the virtual endoscopic image $I_{VE}$ based on the position $P_I$ of the structure of interest identified by the position of interest identifying unit 25, the endoscope position $P_E$ obtained by the endoscope position obtaining unit 22, and the surgical tool position $P_I$ obtained by the surgical tool position obtaining unit 23 (#5). The virtual endoscopic image $I_{VE}$ is an image representing the interior of the abdominal cavity of the subject, where the position $P_I$ of the structure of interest is the view point and the surgical tool position $P_T$ is the center of the field of view. If the endoscope position $P_E$ is present in the field of view of the virtual endoscopic image $I_{VE}$, a shape image representing the surgical tool 6 and a shape image representing the endoscope 1 are combined with the virtual endoscopic image $I_{VE}$.

The display control unit 27 causes the WS display 10 to display the real endoscopic image $I_{RE}$, obtained by the real endoscopic image obtaining unit 21 and the virtual endoscopic image $I_{VE}$ generated by the virtual endoscopic image generating unit 26 side by side on a single screen (#6).

On the image processing workstation 9, operations to obtain a new real endoscopic image $I_{RE}$ (#3), to obtain the endoscope position $P_E$ and the surgical tool position $P_T$ at that point of time (#4), to generate the virtual endoscopic image $I_{VE}$ (#5) and to update the displayed real endoscopic image $I_{RE}$, and virtual endoscopic image $I_{VE}$ (#6) are repeated, unless an operation to instruct to end the observation is made (#7: No). With this, the real endoscopic image $I_{RE}$, and the virtual endoscopic image $I_{VE}$ are continuously displayed on the WS display 10 in a temporally synchronized manner. When the operation to instruct to end the observation is made (#7: Yes), the image processing workstation 9 ends the repeated operations in steps #3 to #6 described above.

Next, details of the operations performed by the individual processing units in the image processing workstation 9 are described.

Figure 5:
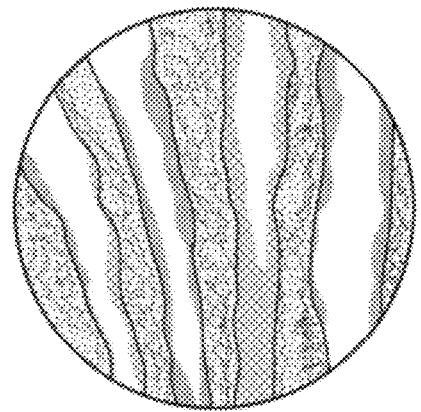
FIG. 5 is a diagram schematically illustrating one example of a real endoscopic image that is displayed in the first embodiment of the invention.

The real endoscopic image obtaining unit 21 is a communication interface that receives the real endoscopic image $I_{RE}$ via communication with the real endoscopic image forming unit (digital processor) 2 and stores the real endoscopic image $I_{RE}$ in a predetermined memory area of the image processing workstation 9. The real endoscopic image $I_{RE}$ is transferred from the real endoscopic image forming unit 2 based on a request from the real endoscopic image obtaining unit 21. FIG. 5 schematically illustrates one example of the real endoscopic image $I_{RE}$.

The endoscope position obtaining unit 22 has a function of a communication interface to obtain the endoscope position $PS_E$ via communication with the endoscope position detecting unit 11, and a function of converting the obtained endoscope position $PS_E$ in the 3D coordinate system of the position sensor 8 into the endoscope position $P_E$ represented by coordinate values in the 3D coordinate system of the 3D medical image V and storing the endoscope position $P_E$ in a predetermined memory area of the image processing workstation 9. With respect to the former communication interface function, the endoscope position $PS_E$ is obtained from the endoscope position detecting unit 11 based on a request from the endoscope position obtaining unit 22. With respect to the latter coordinate transformation function, an amount of rotation of coordinate axes is calculated in advance based on a correspondence relationship between the orientation of each coordinate axis in the 3D coordinate system of the position sensor and the orientation of each coordinate axis in the 3D coordinate system of the 3D medical image V, and coordinate values of a position on the subject corresponding to the origin of the 3D medical image V in the 3D coordinate system of the position sensor 8 are measured in advance to calculate an amount of translation between the coordinate axes based on the coordinate values of the origin. Then, the conversion of the endoscope position $PS_E$ represented by the 3D coordinate system of the position sensor 8 into the endoscope position $P_E$ represented by the coordinate values in the 3D coordinate system of the 3D medical image V can be achieved using a matrix that applies rotation by the calculated amount of rotation and translation by the calculated amount of translation.

Similarly to the endoscope position obtaining unit 22, the surgical tool position obtaining unit 23 has a function of a communication interface to obtain the surgical tool position $PS_T$ via communication with the surgical tool position detecting unit 12, and a function of converting the obtained surgical tool position $PS_T$ in the 3D coordinate system of the position sensor 8 into the surgical tool position $P_T$ represented by the coordinate values in the 3D coordinate system of the 3D medical image V and storing the surgical tool position $P_T$ in a predetermined memory area of the image processing workstation 9.

The 3D medical image obtaining unit 24 has a function of a communication interface to receive the 3D medical image V from the 3D medical image forming unit 5 and store the 3D medical image V in a predetermined memory area of the image processing workstation 9.

The position of interest identifying unit 25 shows, on a cross-sectional image representing a predetermined cross-section generated from the 3D medical image V using the known MPR method, a user interface for receiving an operation to specify the structure of interest via the pointing device or keyboard of the image processing workstation 9. For example, when the pointing device is clicked on the structure of interest shown in the cross-sectional image, the position of interest identifying unit 25 identifies the position $P_I$ of the structure of interest, which has been specified by the click, in the 3D medical image V, and stores the position $P_I$ in a predetermined memory area of the image processing workstation 9. As the structure of interest, a site of surgical interest or a site that requires attention during surgery may be specified, as desired by the user.

Figure 4:
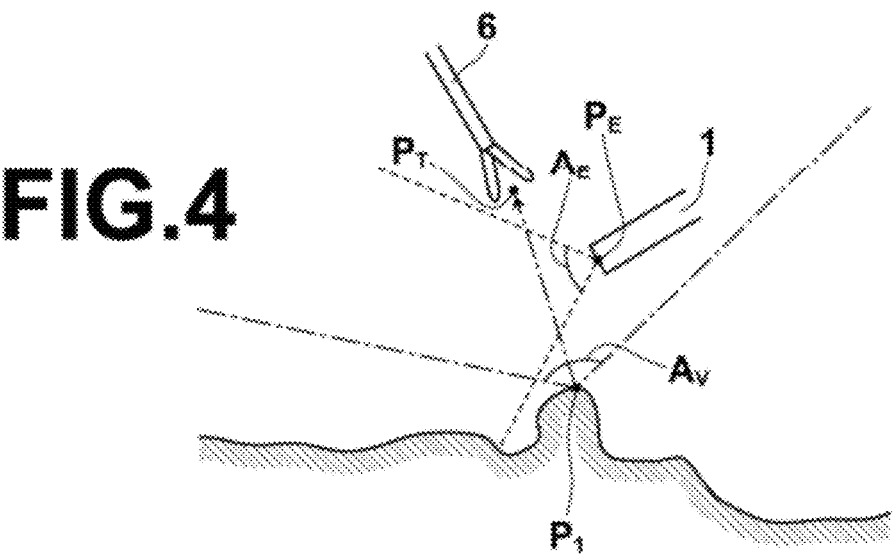
FIG. 4 is a diagram schematically illustrating one example of a positional relationship between a real endoscope, a surgical tool and a structure of interest, and angles of view of the real endoscope and a virtual endoscope.
Figure 6:
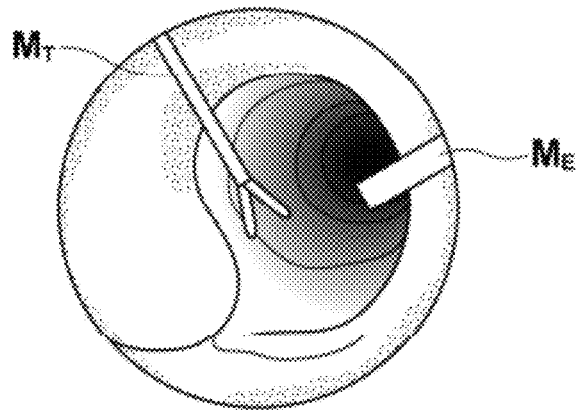
FIG. 6 is a diagram schematically illustrating one example of a virtual endoscopic image that is displayed in the first embodiment of the invention.

The virtual endoscopic image generating unit 26 generates the virtual endoscopic image $I_{VE}$ from the 3D medical image V inputted thereto based on the position $P_I$ of the structure of interest, the endoscope position $P_E$ and the surgical tool position $P_T$. FIG. 4 schematically illustrates one example of a positional relationship among the endoscope 1, the surgical tool 6 and the structure of interest $P_I$, and angles of view of the endoscope 1 and the virtual endoscope. As shown in the drawing, the virtual endoscopic image generating unit 26 uses the position $P_I$ of the structure of interest as the view point and the surgical tool position $P_T$ as the center of the field of view to set a plurality of lines of sight radiating from the view point $P_I$ within the range of an angle of view $A_V$, and generates a preliminary virtual endoscopic image by projecting pixel values along each line of sight by volume rendering using the known perspective projection. The angle of view $A_V$ of the preliminary virtual endoscopic image is set to be wider than an angle of view $A_R$ of the real endoscopic image $I_{RE}$ through startup parameters of the program. For the volume rendering, a color template is used, which defines color and transparency in advance such that an image having almost the same appearance as that of the sites in the abdominal cavity shown in the real endoscopic image $I_{RE}$ is obtained. Further, the virtual endoscopic image generating unit 26 generates a surgical tool shape image $M_T$ showing a state where the surgical tool 6 is present at the surgical tool position $P_T$, and an endoscope shape image $M_E$ showing a state where the endoscope 1 is present at the endoscope position $P_E$ if the endoscope position $P_E$ is present in the field of view of the virtual endoscopic image. Specifically, the surgical tool shape image $M_T$ and the endoscope shape image $M_E$ are generated based on images representing the shapes of the endoscope 1 and the surgical tool 6 stored in a database, as well as the surgical tool position $P_T$ and the endoscope position $P_E$, as taught in the above-mentioned Patent Document 2. Then, the virtual endoscopic image generating unit 26 generates the virtual endoscopic image $I_{VE}$ by combining the preliminary virtual endoscopic image with the surgical tool shape image $M_T$ and the endoscope shape image $M_E$ by a known technique, such as alpha blending. FIG. 6 schematically illustrates one example of the thus generated virtual endoscopic image $I_{VE}$, wherein the shape image $M_T$ representing the surgical tool 6 is superimposed at the surgical tool position $P_T$ at the near center of the field of view, and the shape image $M_E$ representing the endoscope 1 is superimposed at the endoscope position $P_E$ in the field of view, and the image as a whole virtually represents a state where the interior of the abdominal cavity is viewed with an endoscope from the position of the structure of interest $P_I$ shown in FIG. 4 during endoscopic surgery.

The display control unit 27 generates a display screen where the real endoscopic image $I_{RE}$ and the virtual endoscopic image $I_{VE}$ are displayed side by side on a single screen and outputs the generated screen to the WS display 10. In this manner, the display screen where the real endoscopic image $I_{RE}$ schematically shown in FIG. 5 as an example and the virtual endoscopic image $I_{VE}$ schematically shown in FIG. 6 as an example are displayed side by side is displayed on the WS display 10.

As described above, in the first embodiment of the invention, prior to observation of the interior of the abdominal cavity using the endoscope 1, the 3D medical image obtaining unit 24 obtains the 3D medical image V formed by the 3D medical image forming unit 5, and the position of interest identifying unit 25 identifies the position $P_I$ of the structure of interest in the abdominal cavity in the 3D medical image V. During the observation, the real endoscopic image obtaining unit 21 obtains the real endoscopic image $I_{RE}$ formed by the real endoscopic image forming unit 2, and at the same time, the endoscope position obtaining unit 22 obtains the position $P_E$ of the endoscope 1 in the 3D medical image V detected by the endoscope position detecting unit 11 and the surgical tool position obtaining unit 23 obtains the position $P_T$ of the surgical tool 6 in the 3D medical image V detected by the surgical tool position detecting unit 12. Then, the virtual endoscopic image generating unit 26 generates, from the 3D medical image V, the virtual endoscopic image $I_{VE}$, in which the position $P_I$ of the structure of interest is the view point and the surgical tool position $P_T$ is the center of the field of view, and the endoscope 1 and the surgical tool 6 are combined at the endoscope position $P_E$ and the surgical tool position $P_T$, respectively. Then, the display control unit 27 causes the WS display 10 to display the real endoscopic image $I_{RE}$ and the virtual endoscopic image $I_{VE}$. The thus displayed virtual endoscopic image $I_{VE}$ looks like an image taken with a camera that monitors the approach of the endoscope 1 and the surgical tool 6 to the position $P_I$ of the structure of interest. By using the virtual endoscopic image $I_{VE}$ to compensate for the narrow field of view of the real endoscopic image $I_{RE}$, the approach of the endoscope 1 and the surgical tool 6 to the structure of interest can be recognized more reliably, thereby helping to prevent misoperation, or the like, during surgery or examination.

Further, at this time, the field of view of the virtual endoscope of the continuously displayed virtual endoscopic image $I_{VE}$ is changed real-time by feedback of the real-time positions of the endoscope 1 and the surgical tool 6 detected by the endoscope position detecting unit 11 and the surgical tool position detecting unit 12. This allows the user to dynamically and more appropriately recognize the approach of the endoscope 1 and the surgical tool 6 to the structure of interest.

Further, the real endoscopic image forming unit 2 forms the real endoscopic image $I_{RE}$ representing the interior of body cavity taken real-time with the endoscope 1, and the real endoscopic image $I_{RE}$ which is formed almost at the same time when the position of the endoscope 1 or the surgical tool 6 used to generate the virtual endoscopic image $I_{VE}$ is detected is further displayed. The real endoscopic image $I_{RE}$ and the virtual endoscopic image $I_{VE}$ show the state of the interior of the body cavity almost at the same point of time, and the real endoscopic image $I_{RE}$ and the virtual endoscopic image $I_{VE}$ are continuously displayed in a temporally synchronized manner. Further, at this time, the field of view of the real endoscopic image $I_{RE}$ changes along with movement or rotation of the endoscope 1, and the field of view of the virtual endoscopic image $I_{VE}$ changes along with movement of the surgical tool 6. In this manner, in the first embodiment of the invention, the user can observe the interior of body cavity with complementarily using the real endoscopic image $I_{RE}$ and the virtual endoscopic image $I_{VE}$.

Still further, the virtual endoscopic image generating unit 26 generates the virtual endoscopic image $I_{VE}$ using the color template, which defines color and transparency in advance such that an image having almost the same appearance as that of the sites in the abdominal cavity shown in the real endoscopic image $I_{RE}$ is obtained. Therefore, the user can observe both the real endoscopic image $I_{RE}$ and the virtual endoscopic image $I_{VE}$ displayed side by side on the WS display 10 by the display control unit 27 without a feel of inconsistency.

A second embodiment of the invention is a modification of a volume rendering process carried out by the virtual endoscopic image generating unit 26. The hardware configuration, the functional blocks and the overall flow of the process of the endoscopic observation support system of the second embodiment are the same as those in the first embodiment.

Figure 7A:
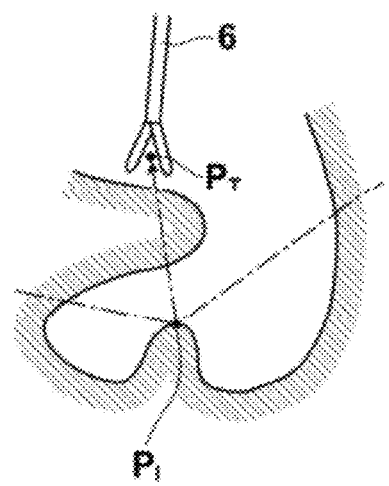
FIG. 7A is a diagram schematically illustrating one example of a positional relationship between a structure of interest and a surgical tool.
Figure 7B:
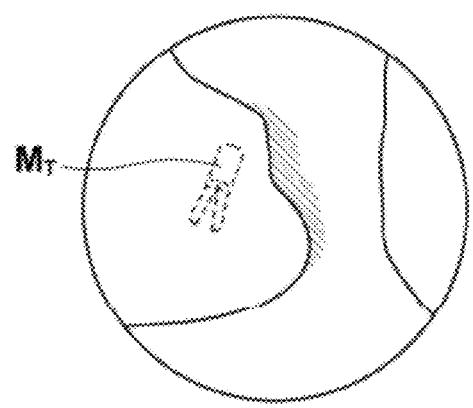
FIG. 7B is a diagram schematically illustrating one example of the virtual endoscopic image that is displayed in the second embodiment of the invention.

FIG. 7A schematically illustrates one example of a positional relationship between the structure of interest and the surgical tool 6. As shown in the drawing, in a case where there is an anatomical structure that obstructs the view between the position $P_I$ of the structure of interest, which is used as the view point of the virtual endoscopic image $I_{VE}$, and the surgical tool position $P_T$, if the color template is defined to provide the anatomical structure with high opacity, the surgical tool 6 behind the anatomical structure is not shown in the virtual endoscopic image $I_{VE}$. Therefore, in the second embodiment of the invention, the virtual endoscopic image generating unit 26 generates the virtual endoscopic image $I_{VE}$ using a color template that defines opacity such that the sites in the body cavity are shown semitransparent. In the thus generated virtual endoscopic image $I_{VE}$, as schematically shown in FIG. 7B, the anatomical structure present between the position $P_I$ of the structure of interest and the surgical tool position $P_T$ is shown semitransparent, and the surgical tool shape image $M_T$ is shown in a visually recognizable manner at a position corresponding to the surgical tool position $P_T$ behind the anatomical structure. Such an image where an anatomical structure in the abdominal cavity is shown semitransparent cannot be formed by the real endoscopic image forming unit 2, and therefore practical value of using the virtual endoscopic image $I_{VE}$ showing such a semitransparent anatomical structure complementarily to the real endoscopic image $I_{RE}$ is very high.

A third embodiment of the invention is also a modification of the volume rendering process carried out by the virtual endoscopic image generating unit 26. The hardware configuration, the functional blocks and the overall flow of the process of the endoscopic observation support system of the third embodiment are the same as those in the first embodiment.

Figure 8A:
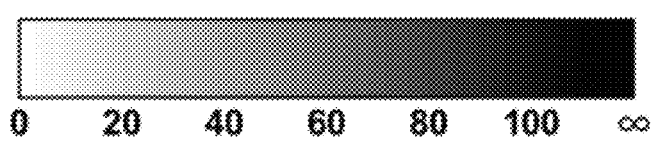
FIG. 8A is a diagram schematically illustrating one example of a color template for changing a display color in the virtual endoscopic image depending on a distance from a view point to the surface of an anatomical structure in the abdominal cavity according to the third embodiment of the invention.
Figure 8B:
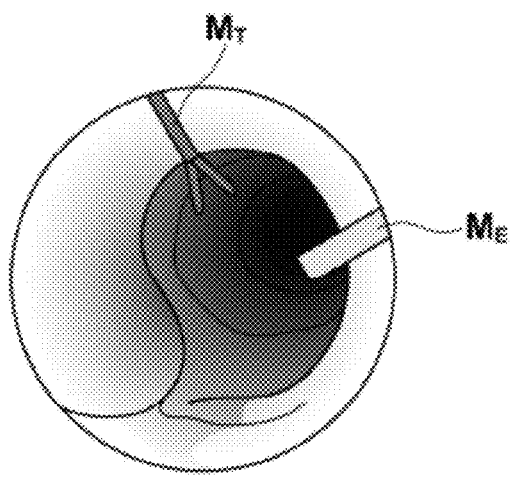
FIG. 8B is a diagram schematically illustrating one example of the virtual endoscopic image, in which the display color is changed depending on the distance from the view point, according to the third embodiment of the invention.

FIG. 8A schematically illustrates one example of the color template used in the third embodiment of the invention. As shown in the drawing, this color template is defined such that the color of the virtual endoscopic image $I_{VE}$ is changed depending on a distance from the view point $P_I$ on the structure of interest to the surface of a structure in the abdominal cavity. For example, the virtual endoscopic image generating unit 26 detects, a position where a change of pixel value along each line of sight of the perspective projection is larger than a predetermined threshold or a position where the pixel value is equal to or larger than a predetermined threshold as the surface of a structure in the abdominal cavity, and calculates the distance from the view point $P_I$ to the surface of the structure in the abdominal cavity. Then, the virtual endoscopic image generating unit 26 uses the color template to determine the pixel value of the detected surface of the structure shown in the virtual endoscopic image $I_{VE}$. The thus generated virtual endoscopic image $I_{VE}$ has a thinner color at the surface of a structure nearer to the position $P_I$ of the structure of interest, and a denser color at the surface of a structure farther from the position $P_I$ of the structure of interest, as schematically shown in FIG. 8B as an example. In this manner, depth perception of the virtual endoscopic image $I_{VE}$, which is hard to be perceived, can be compensated for, thereby facilitating the user to recognize the approach of the endoscope 1 and the surgical tool 6. It should be noted that the color and density of the shape image $M_E$ of the endoscope 1 and the shape image $M_T$ of the surgical tool displayed in the virtual endoscopic image $I_{VE}$ may also be changed depending on the distance from the position $P_I$ of the structure of interest in a manner similar to that described above.

Figure 9:
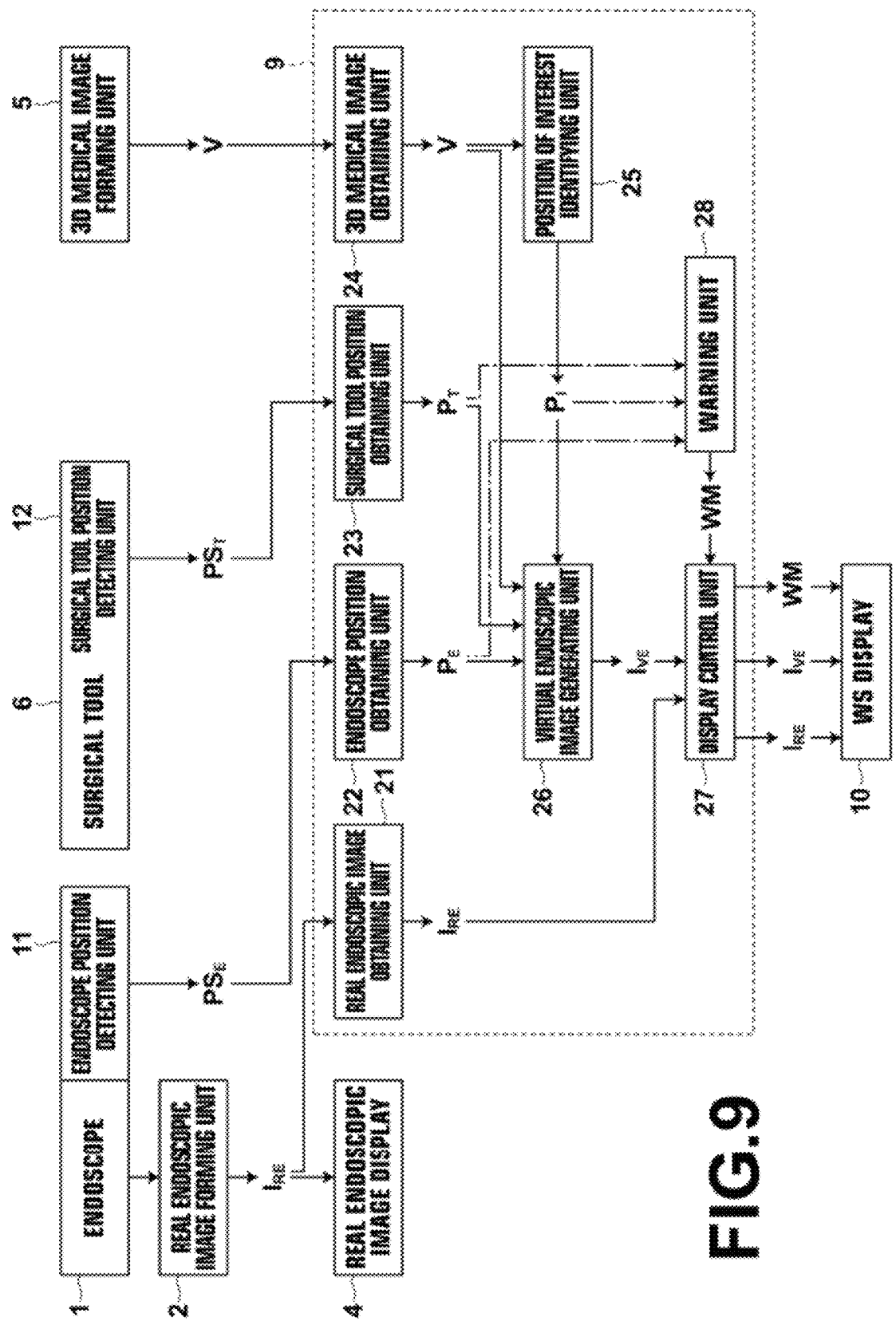
FIG. 9 is a functional block diagram of the endoscopic observation support system according to a fourth embodiment of the invention.

As shown in the functional block diagram of FIG. 9, a fourth embodiment of the invention includes a warning determination unit 28 in addition to the components of the first embodiment. The hardware configuration of the endoscopic observation support system of the fourth embodiment is the same as that in the first embodiment.

The warning determination unit 28 is a processing unit implemented on the image processing workstation 9. The warning determination unit 28 calculates a distance between the endoscope position $P_E$ and the position $P_I$ of the structure of interest and a distance between the surgical tool position $P_T$ and the position $P_I$ of the structure of interest. If either of the calculated distance is smaller than a predetermined threshold, i.e., if the endoscope 1 or the surgical tool 6 approaches too close to the structure of interest, the warning determination unit 28 outputs a warning message WM.

Figure 10:
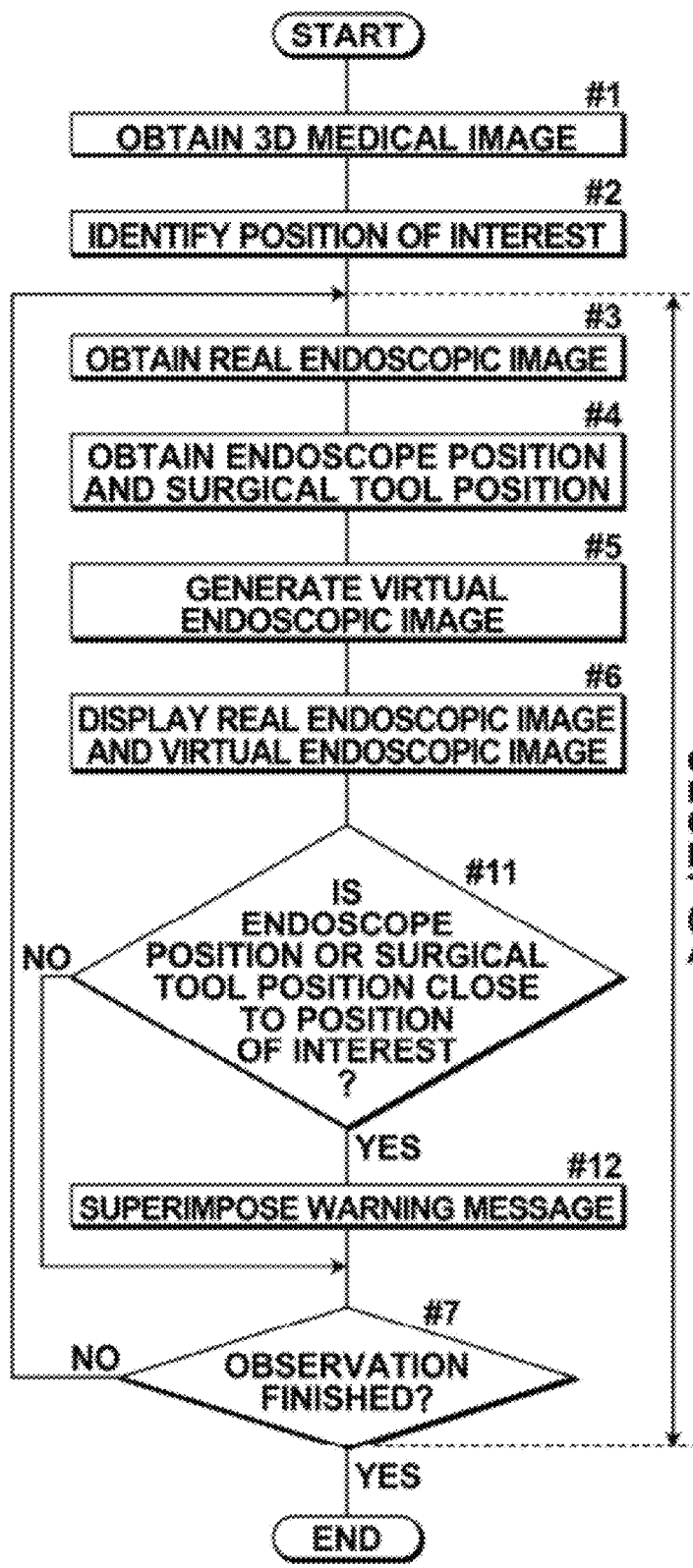
FIG. 10 is a flow chart illustrating the flow of the endoscopic observation support process according to the fourth embodiment of the invention.
Figure 11:
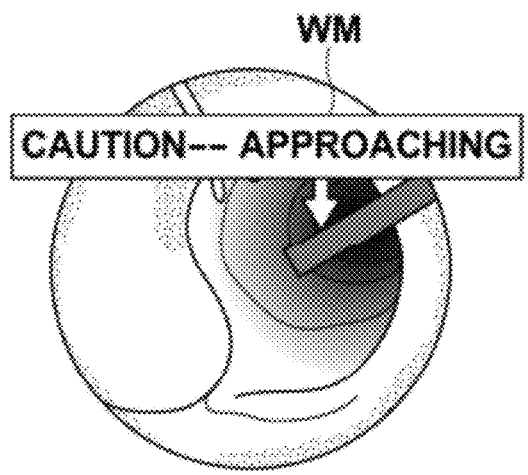
FIG. 11 is a diagram schematically illustrating one example of a warning display according to the fourth embodiment of the invention.

FIG. 10 is a flow chart illustrating the flow of the endoscopic observation support process according to the fourth embodiment of the invention. As shown in the drawing, after the real endoscopic image $I_{RE}$ and the virtual endoscopic image $I_{VE}$ are displayed in step #6 of the first embodiment, the warning determination unit 28 compares each of the above-described distances with the threshold (#11). If either of the above-described distances is smaller than the threshold (#11: Yes), the warning determination unit 28 outputs the warning message WM, and the display control unit 27 superimposes an arrow mark with a comment "CAUTION—APPROACHING" in the vicinity of the displayed endoscope 1 or the surgical tool 6 (the endoscope 1 is shown in the drawing) that is too close to the structure of interest, and shows the shape image representing the endoscope 1 or surgical tool in a denser display color, as shown in FIG. 11 as an example. This facilitates the user to recognize the abnormal approach of the endoscope 1 or the surgical tool 6 to the structure of interest, thereby helping to prevent misoperation of the endoscope 1 and the surgical tool 6. Such a warning display is particularly effective when a blood vessel, or the like, which will cause massive bleeding if it is damaged during surgery, is specified as the structure of interest at the position of interest identifying unit 25.

Besides being superimposed on the displayed virtual endoscopic image $I_{VE}$, as described above, the warning message may be outputted in the form of a warning sound or voice, or may be outputted both as the superimposed warning message and the warning sound. Further, a risk determination table that defines a risk depending on the distance in a stepwise manner may be prepared in advance, and the warning determination unit 28 may reference the risk determination table based on the calculated distance to determine the risk, and the determined value of the risk may be outputted as the warning message WM and the display control unit 27 may display an icon, or the like, corresponding to the risk on the WS display 10.

Figure 12:
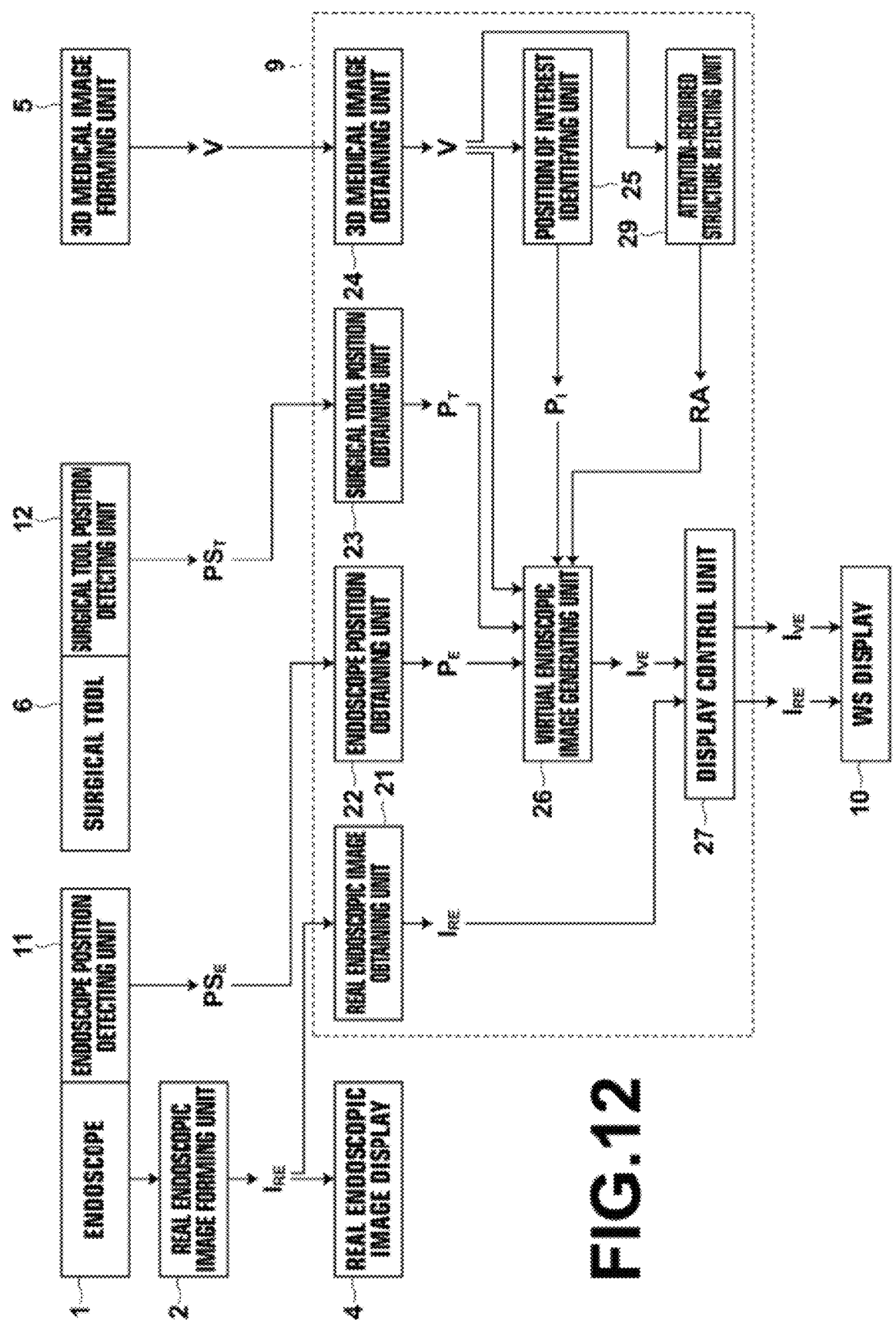
FIG. 12 is a functional block diagram of the endoscopic observation support system according to a fifth embodiment of the invention.

As shown in the functional block diagram of FIG. 12, a fifth embodiment of the invention includes an attention-required structure detecting unit 29 in addition to the components of the first embodiment. The hardware configuration of the endoscopic observation support system is the same as that of the first embodiment.

Figure 14A:
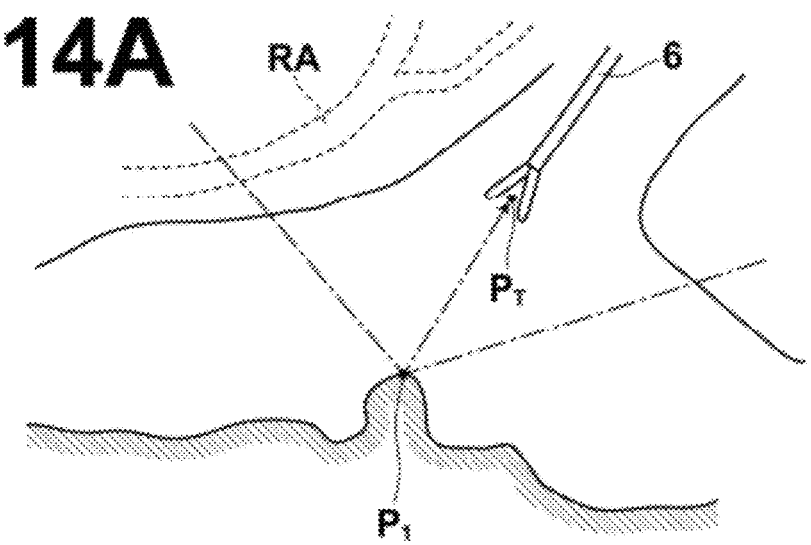
FIG. 14A is a diagram schematically illustrating one example of a positional relationship between a structure of interest and a structure that requires attention.

The attention-required structure detecting unit 29 is a processing unit implemented on the image processing workstation 9. The attention-required structure detecting unit 29 detects a region of attention-required structure RA from the 3D medical image V inputted thereto using a known image recognition technique. FIG. 14A schematically illustrates one example of a positional relationship between the structure of interest and the attention-required structure. In this example, the attention-required structure detecting unit 29 detects an attention-required blood vessel region RA that is located behind the abdominal wall by performing known blood vessel extraction processing.

Figure 14B:
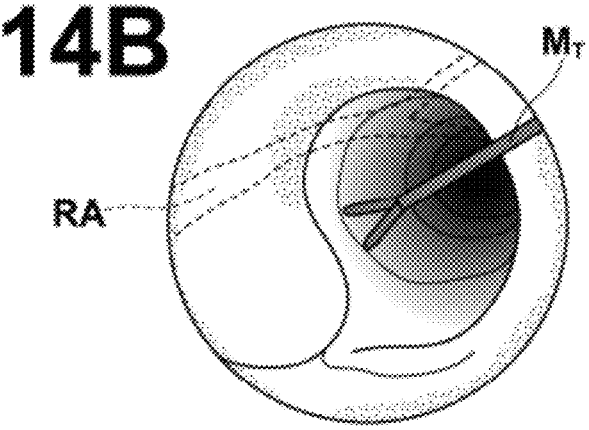
FIG. 14B is a diagram schematically illustrating one example of the virtual endoscopic image that is displayed in the fifth embodiment of the invention.

FIG. 13 is a flow chart illustrating the flow of the endoscopic observation support process according to the fifth embodiment of the invention. As shown in the drawing, after the position of interest $P_I$ is identified in step #2 of the first embodiment, the attention-required structure detecting unit 29 detects the region of attention-required structure RA (#13). In step #5, the virtual endoscopic image generating unit 26 generates the virtual endoscopic image $I_{VE}$ using a color template that is defined to show the region of attention-required structure RA in a visually recognizable manner. FIG. 14B schematically illustrates one example of the generated virtual endoscopic image $I_{VE}$. The virtual endoscopic image $I_{VE}$ shown in the drawing is generated using a color template that defines color and opacity such that pixels representing the abdominal wall are shown semitransparent to increase the visual recognizability of pixels representing the blood vessel. This increases the visual recognizability of the attention-required structure, thereby helping to prevent misoperation of the endoscope 1 and the surgical tool 6, similarly to the fourth embodiment.

It should be noted that the attention-required structure detecting unit 29 may detect the region of attention-required structure RA via manual operation by the user. Further, a marker, such as an arrow, and an annotation, such as a text comment, may be superimposed on the region of attention-required structure RA.

In a sixth embodiment of the invention, the 3D medical image V is formed and obtained real-time during the observation using the endoscope. In this case, the endoscope marker 7a, the surgical tool marker 7b and the position sensor 8 in the hardware configuration of the first embodiment (see FIG. 1) are not necessary.

Figure 15:
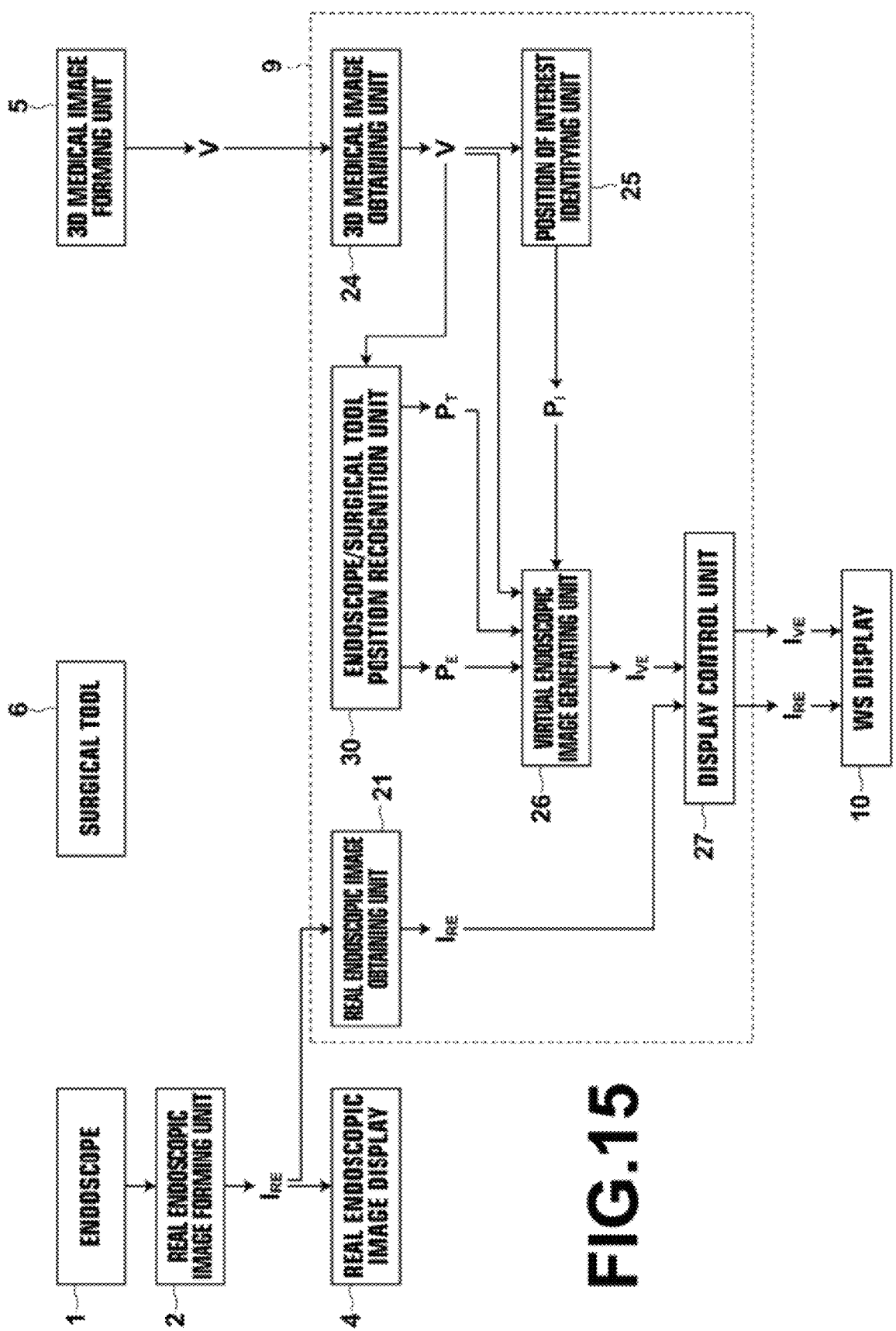
FIG. 15 is a functional block diagram of the endoscopic observation support system according to a sixth embodiment of the invention.

FIG. 15 is a functional block diagram of the endoscopic observation support system according to the sixth embodiment of the invention. As shown in the drawing, the endoscopic observation support system of the sixth embodiment includes an endoscope/surgical tool position recognition unit 30 in place of the endoscope position detecting unit 11, the surgical tool position detecting unit 12, the endoscope position obtaining unit 22 and the surgical tool position obtaining unit 23 of the first embodiment. That is, the endoscope/surgical tool position recognition unit 30 corresponds to the position detecting means of the invention.

The endoscope/surgical tool position recognition unit 30 is a processing unit implemented on the image processing workstation 9. The endoscope/surgical tool position recognition unit 30 extracts an area showing the endoscope 1 or the surgical tool 6 from the 3D medical image V inputted thereto using known pattern recognition processing to recognize the endoscope position $P_E$ and the surgical tool position $P_T$.

Figure 16:
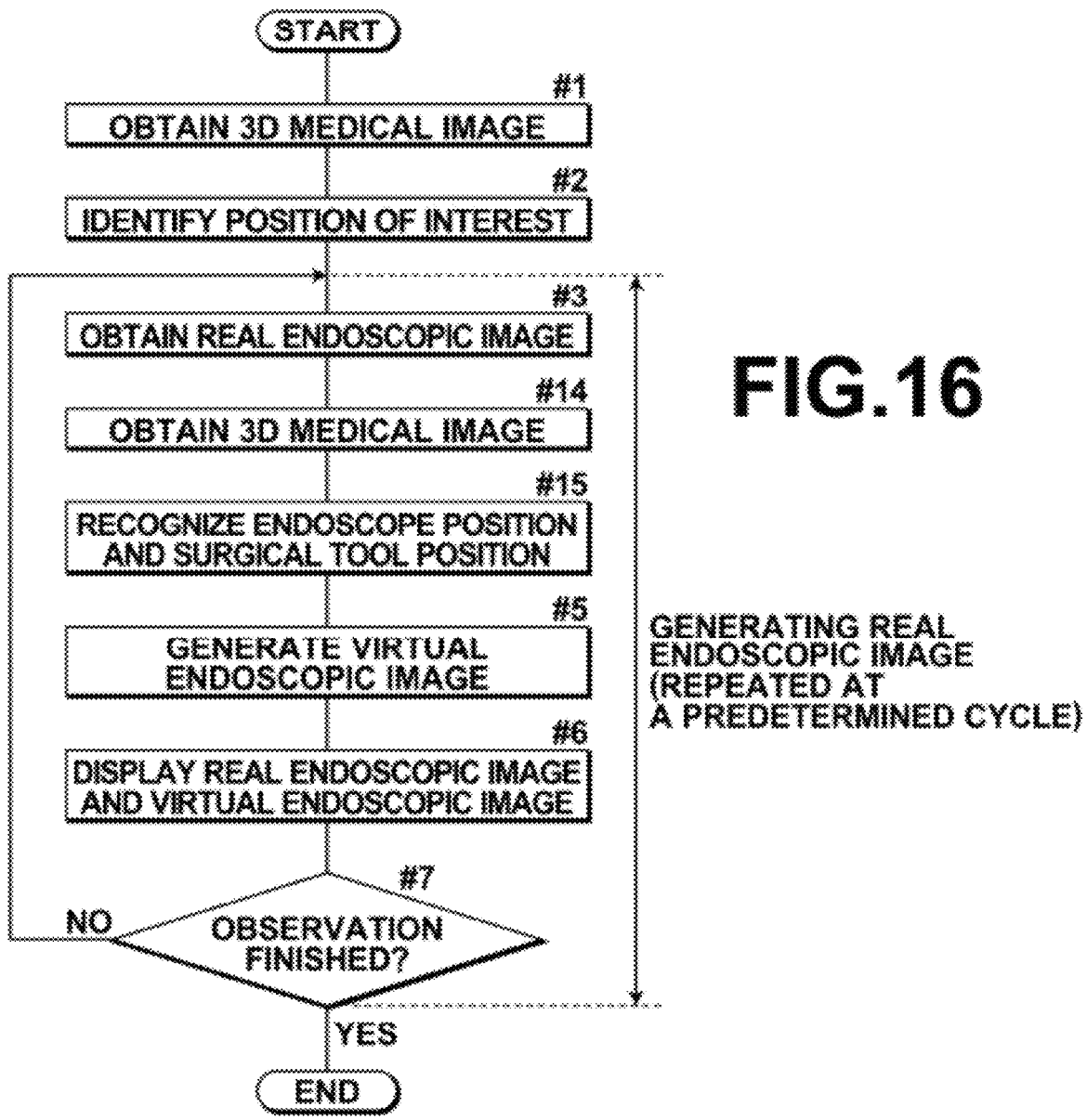
FIG. 16 is a flow chart illustrating the flow of the endoscopic observation support process according to the sixth embodiment of the invention.

FIG. 16 is a flow chart illustrating the flow of the endoscopic observation support process according to the sixth embodiment of the invention. As shown in the drawing, after the real endoscopic image $I_{RE}$ is obtained in step #3 of the first embodiment, the 3D medical image obtaining unit 24 obtains the 3D medical image V (#14), and the endoscope/surgical tool position recognition unit 30 recognizes the endoscope position $P_E$ and the surgical tool position $P_T$ based on the 3D medical image V obtained by the 3D medical image obtaining unit 24 (#15). In step #5, the virtual endoscopic image generating unit 26 generates the virtual endoscopic image $I_{VE}$ using a color template that is defined such that the area showing the endoscope 1 or the surgical tool 6 extracted by the endoscope/surgical tool position recognition unit 30 is displayed in a predetermined color. Therefore, it is not necessary to generate the shape images of the endoscope 1 and the surgical tool 6 as in the first embodiment. By forming and obtaining the 3D medical image V real-time during the observation using the endoscope in this manner, the obtained 3D medical image V shows the state of the interior of the abdominal cavity almost at the same point of time as that shown in the real endoscopic image $I_{RE}$. Therefore, the generated virtual endoscopic image $I_{VE}$ more accurately shows the real-time state of the interior of the abdominal cavity than a case where the 3D medical image V obtained before the observation using the endoscope is used. It should be noted that, when the 3D medical image V is taken in steps #1 and #14 in this embodiment, it is necessary to pay attention to the posture of the subject during imaging so that the position of the subject corresponding to the origin of the coordinate axes and the orientation of the coordinate axes are not changed.

In the sixth embodiment of the invention, it is preferable to use an ultrasound diagnostic device as the modality 5, in view of reducing radiation exposure of the subject.

The above-described embodiments are merely examples and should not be construed as limiting the technical scope of the invention.

Further, variations and modifications made to the system configuration, the hardware configuration, the process flow, the module configuration, the user interface and the specific contents of the process of the above-described embodiments without departing from the scope and spirit of the invention are also within the technical scope of the invention.

For example, with respect to the system configuration, although the modality 5 is directly connected to the image processing workstation 9 in the hardware configuration of FIG. 1 of the above-described embodiments, an image storage server may be connected to the LAN and the 3D medical image V formed by the modality 5 may once be stored in a database of the image storage server, so that the 3D medical image V is transferred from the image storage server to the image processing workstation 9 in response to a request from the image processing workstation 9.

The endoscope 1 may not be a hard endoscope, and a soft endoscope or a capsular endoscope may be used.

As the modality 5, besides the above-mentioned CT device and the ultrasound diagnostic device, a MRI device, etc., may be used.

The WS display 10 may be a display that supports known stereoscopic display to display the virtual endoscopic image $I_{VE}$ which is a stereoscopic image. For example, in a case where the WS display 10 is a display device that achieves stereoscopic display using two parallax images for right and left eyes, the virtual endoscopic image generating unit 26 may generate virtual endoscope parallax images for right and left eyes by setting positions of right and left eyes, which are shifted from the position $P_I$ of the structure of interest by an amount of parallax between the right and left eyes, and performing perspective projection with using the thus set right and left eye positions as the view points. Then, the display control unit 27 may exert control such that display pixels of the WS display 10 for the left eye to display the virtual endoscope parallax image for the left eye and display pixels of the WS display 10 for the right eye to display the virtual endoscope parallax image for the right eye.

The endoscope position detecting unit 11 and the surgical tool position detecting unit 12 may use a magnetic system, or may use a gyro or a rotary encoder, as taught in Patent Document 2.

The body site to be observed may be a site of the subject which is suitable for observation using an endoscope, such as the interior of the thoracic cavity, other than the interior of the abdominal cavity.

In the above-described embodiments, the image processing workstation 9 receives the image based on a request from the real endoscopic image obtaining unit 21 with taking the communication load into account, assuming that a cycle at which the real endoscopic image forming unit 2 forms the real endoscopic image $I_{RE}$ is shorter than a cycle at which the virtual endoscopic image generating unit 26 generates the virtual endoscopic image $I_{VE}$. However, the real endoscopic image obtaining unit 21 may receive all the real endoscopic images IE sequentially formed by the real endoscopic image forming unit 2. In this case, the display control unit 27 may update the displayed real endoscopic image $I_{RE}$ on the WS display 10 each time the real endoscopic image $I_{RE}$ is received, asynchronously with the timing of generation of the virtual endoscopic image $I_{VE}$ by the virtual endoscopic image generating unit 26.

The endoscope position obtaining unit 22 may receive all the endoscope positions $PS_E$ detected at predetermined time intervals by the endoscope position detecting unit 11, and may convert only the endoscope position $PS_E$ which is received at the time when the operation in step #4 of FIG. 3 is invoked into the endoscope position $P_E$ by the coordinate transformation function to output it. The same applies to the surgical tool position obtaining unit 23.

The coordinate transformation carried out by the endoscope position obtaining unit 22 and the surgical tool position obtaining unit 23 in the above-described embodiments may be carried out by the virtual endoscopic image generating unit 26.

The position of interest identifying unit 25 may automatically identify the position of interest using a known image recognition technique (such as a technique for extracting blood vessels or an organ or a technique for detecting an abnormal shadow).

The virtual endoscopic image generating unit 26 may set the endoscope position $P_E$ at the center of the field of view so that the endoscope 1 is always within the field of view, in place of setting the surgical tool position $P_T$ at the center of the field of view so that the surgical tool 6 is always within the field of view. Further alternatively, an internally dividing point of the segment $P_E$-$P_T$, such as a midpoint between the endoscope position $P_E$ and the surgical tool position $P_T$, may be set at the center of the field of view, and the angle of view may be set such that both the endoscope 1 and the surgical tool 6 are within the field of view. Still alternatively, the angle of view and a magnification factor may be adjusted depending on distances between the position $P_T$ of the structure of interest, the endoscope position $P_E$ and the surgical tool position $P_T$. For example, if the distances between these positions are small, the angle of view may be set narrower and the magnification factor may be set larger than those when the distances between these positions are large, so that the area in the field of view is magnified to facilitate the observation.

In place of combining the shape image representing the endoscope 1 or the surgical tool 6 with the virtual endoscopic image $I_{VE}$, a marker, such as an arrow, may be displayed at the endoscope position $P_E$ or the surgical tool position $P_T$.

The virtual endoscopic image generating unit 26 may generate the virtual endoscopic images $I_{VE}$ viewed from a plurality of view points by setting a plurality of positions of interest, such as a site of surgical interest, an attention-required blood vessel and an attention-required organ, as the view points.

Figure 17A:
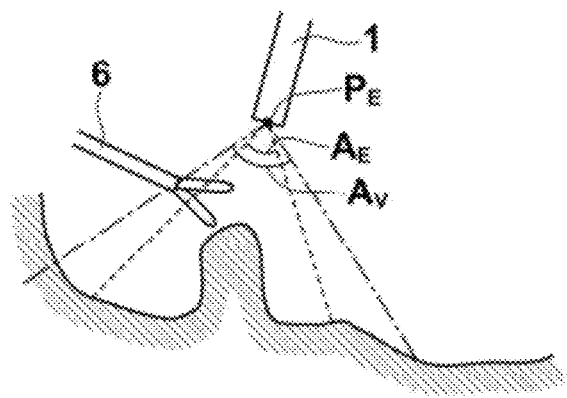
FIG. 17A is a diagram schematically illustrating angles of view of the real endoscopic image and the virtual endoscopic image when the images are combined.
Figure 17B:
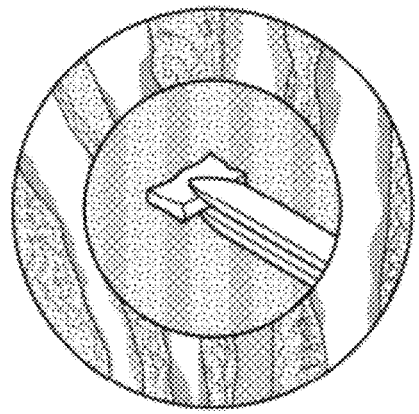
FIG. 17B is a diagram schematically illustrating one example of a composite image generated by combining the real endoscopic image and the virtual endoscopic image.

The image processing workstation 9 may generate and display an image other than the above-described real endoscopic image $I_{RE}$ and virtual endoscopic image $I_{VE}$. For example, a virtual endoscopic image with a wider angle of view $A_V$ than the angle of view $A_E$ of the endoscope 1, as schematically shown in FIG. 17A as an example, may further be generated with setting the endoscope position $P_E$ as the view point and using a magnification factor that renders the size of an object of interest in the image almost the same size as that in the real endoscopic image $I_{RE}$, and a new image, as schematically shown in FIG. 17B as an example, where the real endoscopic image is superimposed on the thus generated virtual endoscopic image with aligning the center of the field of view, i.e., the endoscope position $P_E$, may be generated and displayed.

Figure 18A:
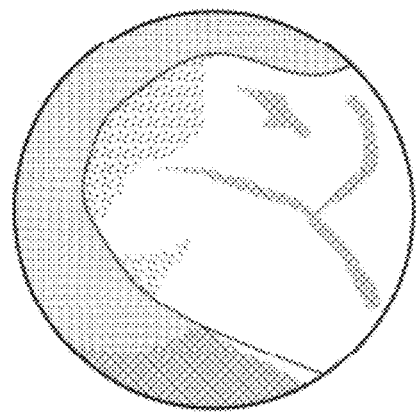
FIG. 18A is a diagram schematically illustrating another example of the real endoscopic image.
Figure 18B:
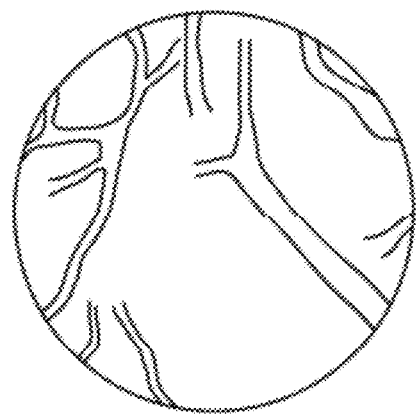
FIG. 18B is a diagram schematically illustrating one example of the virtual endoscopic image, which shows only blood vessels.
Figure 18C:
FIG. 18C is a diagram schematically illustrating one example of a superimposed image of the real endoscopic image and the virtual endoscopic image.

Alternatively, a composite image of the real endoscopic image and the virtual endoscopic image may be generated. For example, a virtual endoscopic image showing only a visualized blood vessel structure, as schematically shown in FIG. 18B as an example, may be combined with a real endoscopic image, as schematically shown in FIG. 18A as an example, to generate a real endoscopic image with the emphasized blood vessel structure, as schematically shown in FIG. 18C as an example.

The invention claimed is:

1. An endoscopic observation support system comprising:
   a 3D medical image forming unit configured to form a 3D medical image representing an interior of a body cavity of a subject;
   a position of interest identifying unit configured to identify a position of a structure of interest in the body cavity in the 3D medical image, the structure of interest being a site of surgical interest or an anatomical structure that requires attention during endoscopic surgery;

a position detecting unit configured to detect a real-time position of at least one of an endoscope and a surgical tool inserted in the body cavity;

a virtual endoscopic image generating unit configured to generate, from the 3D medical image inputted thereto, a virtual endoscopic image representing the interior of the body cavity viewed from a view point, based on the identified position of the structure of interest and the detected position of at least one of the endoscope and the surgical tool in the 3D medical image, wherein the view point is the position of the structure of interest, the position of at least one of the endoscope and the surgical tool is contained in a field of view of the virtual endoscopic image, and the position of at least one of the endoscope and the surgical tool is shown in an identifiable manner in the virtual endoscopic image; and a display control unit configured to cause a display unit to display the virtual endoscopic image.

2. The endoscopic observation support system as claimed in claim 1, further comprising a real endoscopic image forming unit configured to form a real endoscopic image representing the interior of body cavity by real-time imaging with the endoscope, wherein the display control unit further causes the real endoscopic image which is formed almost at the same time when the position of at least one of the endoscope and the surgical tool used to generate the virtual endoscopic image is detected to be displayed.

3. The endoscopic observation support system as claimed in claim 1, wherein the virtual endoscopic image generating unit determines pixel values of the virtual endoscopic image depending on a distance from the structure of interest to a surface of a structure in the body cavity.

4. The endoscopic observation support system as claimed in claim 1, further comprising a warning unit configured to show a warning when an approach of at least one of the endoscope and the surgical tool to the structure of interest satisfies a predetermined criterion.

5. The endoscopic observation support system as claimed in claim 1, wherein the virtual endoscopic image generating unit determines pixel values of the virtual endoscopic image using a color template, wherein the color template is defined to provide the virtual endoscopic image showing sites in the body cavity in almost the same appearance as those shown in a real endoscopic image obtained by imaging with the endoscope.

6. The endoscopic observation support system as claimed in claim 1, further comprising a second structure of interest detecting unit configured to detect a second structure of interest in the body cavity in the 3D medical image, wherein the virtual endoscopic image generating unit generates the virtual endoscopic image in which the second structure of interest is shown in a visually recognizable manner.

7. The endoscopic observation support system as claimed in claim 6, wherein the structure of interest is a site of surgical interest during endoscopic surgery using the endoscope and the second structure of interest is an anatomical structure that requires attention during the endoscopic surgery.

8. The endoscopic observation support system as claimed in claim 1, wherein the position of the endoscope is contained in a field of view of the virtual endoscopic image, and the position of the endoscope is shown in an identifiable manner in the virtual endoscopic image.

9. An endoscopic observation support method comprising the steps of:

forming a 3D medical image representing an interior of a body cavity of a subject before or during observation of the interior of the body cavity with an endoscope inserted in the body cavity;

identifying a position of a structure of interest in the body cavity in the 3D medical image, the structure of interest being a site of surgical interest or an anatomical structure that requires attention during endoscopic surgery;

detecting a real-time position of at least one of the endoscope and a surgical tool inserted in the body cavity;

generating, from the 3D medical image inputted, a virtual endoscopic image representing the interior of the body cavity viewed from a view point, based on the identified position of the structure of interest and the detected position of at least one of the endoscope and the surgical tool in the 3D medical image, wherein the view point is the position of the structure of interest, the position of at least one of the endoscope and the surgical tool is contained in a field of view of the virtual endoscopic image, and the position of at least one of the endoscope and the surgical tool is shown in an identifiable manner in the virtual endoscopic image; and displaying the virtual endoscopic image.

10. The endoscopic observation support method as claimed in claim 9, wherein the position of the endoscope is contained in a field of view of the virtual endoscopic image, and the position of the endoscope is shown in an identifiable manner in the virtual endoscopic image.

11. An endoscopic observation support device comprising:

a 3D medical image obtaining unit configured to obtain a 3D medical image representing an interior of a body cavity of a subject;

a position of interest identifying unit configured to identify a position of a structure of interest in the body cavity in the 3D medical image, the structure of interest being a site of surgical interest or an anatomical structure that requires attention during endoscopic surgery;

a position obtaining unit configured to obtain a real-time position of at least one of an endoscope and a surgical tool inserted in the body cavity detected by a position detecting unit;

a virtual endoscopic image generating unit configured to generate, from the 3D medical image inputted thereto, a virtual endoscopic image representing the interior of the body cavity viewed from a view point, based on the identified position of the structure of interest and the detected position of at least one of the endoscope and the surgical tool in the 3D medical image, wherein the view point is the position of the structure of interest, the position of at least one of the endoscope and the surgical tool is contained in a field of view of the virtual endoscopic image, and the position of at least one of the endoscope and the surgical tool is shown in an identifiable manner in the virtual endoscopic image; and a display control unit configured to cause a display unit to display the virtual endoscopic image.

12. The endoscopic observation support device as claimed in claim 11, wherein the position of the endoscope is contained in a field of view of the virtual endoscopic image, and the position of the endoscope is shown in an identifiable manner in the virtual endoscopic image.

13. A non-transitory computer readable medium containing an endoscopic observation support program for causing a computer to carry out the steps of:
  obtaining a 3D medical image representing an interior of a body cavity of a subject;
  identifying a position of a structure of interest in the body cavity in the 3D medical image, the structure of interest being a site of surgical interest or an anatomical structure that requires attention during endoscopic surgery;
  obtaining a real-time position of at least one of an endoscope and a surgical tool inserted in the body cavity detected by a position detecting unit;
  generating, from the 3D medical image inputted, a virtual endoscopic image representing the interior of the body cavity viewed from a view point, based on the identified position of the structure of interest and the detected position of at least one of the endoscope and the surgical tool in the 3D medical image, wherein the view point is the position of the structure of interest, the position of at least one of the endoscope and the surgical tool is contained in a field of view of the virtual endoscopic image, and the position of at least one of the endoscope and the surgical tool is shown in an identifiable manner in the virtual endoscopic image; and
  causing a display unit to display the virtual endoscopic image.

14. The non-transitory computer readable medium as claimed in claim 13, wherein the position of the endoscope is contained in a field of view of the virtual endoscopic image, and the position of the endoscope is shown in an identifiable manner in the virtual endoscopic image.

\* \* \* \* \*